United States Patent [19]

Thorsteinson et al.

[11] Patent Number: 5,187,140
[45] Date of Patent: Feb. 16, 1993

[54] ALKYLENE OXIDE CATALYSTS CONTAINING HIGH SILVER CONTENT

[75] Inventors: Erlind M. Thorsteinson; Madan M. Bhasin, both of Charleston; Seyed R. Seyedmonir, Cross Lanes, all of W. Va.

[73] Assignee: Union Carbide Chemicals & Plastics Technology Corporation, Danbury, Conn.

[21] Appl. No.: 556,828

[22] Filed: Jul. 23, 1990

Related U.S. Application Data

[63] Continuation-in-part of Ser. No. 423,197, Oct. 18, 1989, abandoned.

[51] Int. Cl.$^5$ .............................................. B01J 23/50
[52] U.S. Cl. .................................... 502/348; 502/226; 502/231; 502/340; 502/344; 549/534
[58] Field of Search ............... 502/347, 348, 344, 341, 502/224, 226, 231

[56] References Cited

U.S. PATENT DOCUMENTS

| | | | |
|---|---|---|---|
| 2,219,575 | 10/1940 | McNamee et al. | 260/348 |
| 2,593,100 | 4/1952 | Calingaert | 252/463 |
| 2,671,764 | 3/1954 | Sacken . | |
| 3,207,700 | 9/1965 | Saffer . | |
| 3,664,970 | 5/1972 | DeMaio . | |
| 3,775,346 | 11/1973 | Calcagno et al. . | |
| 4,007,135 | 2/1977 | Hayden et al. | 502/348 |
| 4,033,903 | 7/1977 | Maxwell . | |
| 4,168,247 | 9/1979 | Hayden et al. . | |
| 4,207,210 | 6/1980 | Kilty . | |
| 4,242,235 | 12/1980 | Cognion et al. . | |
| 4,342,667 | 8/1982 | Armstrong et al. . | |
| 4,368,144 | 1/1983 | Mitsuhata et al. . | |
| 4,376,209 | 3/1983 | Watanabe et al. . | |
| 4,389,338 | 6/1983 | Mitsuhata et al. . | |
| 4,419,276 | 12/1983 | Bhasin et al. | 502/347 |
| 4,455,392 | 6/1984 | Warner et al. | 502/347 |
| 4,645,754 | 2/1987 | Tamura et al. . | |
| 4,717,703 | 1/1988 | Cognion et al. | 502/348 |
| 4,761,394 | 8/1988 | Lauritzen . | |
| 4,769,358 | 9/1988 | Kishimoto et al. . | |
| 4,812,437 | 3/1989 | Nojiri et al. . | |
| 4,820,675 | 4/1989 | Lauritzen | 502/317 |
| 4,829,043 | 5/1989 | Boehning et al. . | |
| 4,831,162 | 5/1989 | Nakajima et al. . | |
| 4,908,343 | 3/1990 | Bhasin . | |

FOREIGN PATENT DOCUMENTS 0243966 11/1987 European Pat. Off. .
0271814 12/1987 European Pat. Off. .
2190855 12/1987 United Kingdom .

OTHER PUBLICATIONS

European Patent Application 0 327 356, filed Feb. 2, 1989.

*Primary Examiner*—Anthony McFarlane
*Attorney, Agent, or Firm*—J. B. Mauro

[57] ABSTRACT

Catalysts for the epoxidation of alkene, especially ethylene, to the corresponding alkylene oxide, e.g., ethylene oxide, which catalysts contain a high silver content on carriers having a high surface area and a high pore volume are disclosed. Methods for making and using such catalysts are also disclosed.

36 Claims, No Drawings

1

ALKYLENE OXIDE CATALYSTS CONTAINING HIGH SILVER CONTENT

FIELD OF THE INVENTION

This is a continuation-in-part of U.S. patent application Ser. No. 423,197, filed Oct. 18, 1989, now abandoned, herein incorporated by reference.

This invention pertains to the field of silver-containing, supported catalysts for the epoxidation of alkene, especially ethylene, to the corresponding alkylene oxide, e.g., ethylene oxide, which catalysts contain a high silver content on carriers having a high surface area and a high pore volume.

BACKGROUND OF THE INVENTION

Ethylene oxide is commercially produced by the epoxidation of ethylene over silver-containing catalysts at elevated temperature. Considerable research efforts have been devoted to providing catalysts that increase the efficiency, or selectivity, of the process to ethylene oxide.

The manufacture of ethylene oxide by the reaction of oxygen or oxygen-containing gases with ethylene in the presence of a silver catalyst is an old and developed art. For example, U.S. Pat. No. 2,040,782, patented May 12, 1936, describes the manufacture of ethylene oxide by the reaction of oxygen with ethylene in the presence of silver catalysts which contain a class of metal promoters. In Reissue U.S. Pat. No. 20,370, dated May 18, 1937, Leforte discloses that the formation of olefin oxides may be effected by causing olefins to combine directly with molecular oxygen in the presence of a silver catalyst. From that point on, the prior art has focused its efforts on improving the catalyst's efficiency in producing ethylene oxide.

Several terms are commonly used to describe some of the parameters of the catalytic system. For instance, "conversion" has been defined as the percentage of alkene or oxygen fed to the reactor which undergoes reaction. The "efficiency" or, as it is sometimes called, the "selectivity" of the overall process is an indication of the proportion, usually represented by a percentage, of the converted material or product which is alkene oxide. The commercial success of a reaction system depends in large measure on the efficiency of the system. Even a very small increase in efficiency will provide substantial cost benefits in large-scale operation. The product of the efficiency and the conversion is equal to the yield, or the percentage of the alkene fed that is converted into the corresponding oxide.

The "activity" of the catalyst is a term used to indicate the amount of alkene oxide contained in the outlet stream of the reactor relative to that in the inlet stream. Activity is generally expressed in terms of pounds of alkene oxide produced per cubic foot of catalyst per hour at specified reaction conditions and rate of feeds. The activity may also be stated in terms of the amount of alkylene oxide in the outlet stream or the difference between the alkylene oxide content of the inlet and outlet streams.

If the activity of a reaction system is low, then, all other things being equal, the commercial value of that system will be low. The lower the activity of a reaction system, the less product produced in a unit time for a given feed rate, reactor temperature, catalyst, surface area, et cetera. A low activity can render even a high efficiency process commercially impractical.

In some instances, activity is measured over a period of time in terms of the amount of alkylene oxide produced at a specified constant temperature. Alternatively, activity may be measured as a function of the temperature required to sustain production of a specified constant amount of alkylene oxide. The useful life of a reaction system is the length of time that reactants can be passed through the reaction system during which acceptable activity is observed.

Deactivation, as used herein, refers to a permanent loss of activity, i.e., a decrease in activity which cannot be recovered. As noted above, activity can be increased by raising the temperature, but the need to operate at a higher temperature to maintain a particular activity is representative of deactivation. Furthermore, catalysts tend to deactivate more rapidly when reaction is carried out at higher temperatures.

To be considered satisfactory, a catalyst must not only have a sufficient activity and the catalytic system provide an acceptable efficiency, but the catalyst must also demonstrate a minimum useful life or stability. When a catalyst is spent, typically the reactor must be shut down and partially dismantled to remove the spent catalyst. This results in losses in time and productivity. In addition, the catalyst must be replaced and the silver salvaged or, where possible, regenerated. Even when a catalyst is capable of regeneration in situ, generally production must be halted for some period of time. At best, replacement or regeneration of catalyst requires additional losses in time to treat the spent catalyst and, at worst, requires replacement of the catalyst with the associated costs.

Since even small improvements in activity, efficiency or useful life may have significance in large scale commercial production, such improvements have been the object of a great deal of research in the direct epoxidation of alkenes. The focus of attempts to improve performance, such as the activity and useful life of the catalyst and the efficiency of the system, has included such areas as feedstream additives or removal of components therefrom; methods of preparation of the catalyst; deposition or impregnation of a particular type or form of silver; composition, formation, physical properties and morphology of the support; additives deposited on or impregnated in the support; shape of support aggregates used in the reactor; and various types of reactors and bed designs, such as stationary and fluidized beds.

In general, the major thrusts in silver catalysts for alkylene epoxidation have been in the fields of promoter and modifier components for the catalytic system. Little attention has been given to the amount of silver contained in the catalysts. Indeed, the amount of silver in a catalyst has often been considered to be an economic trade-off. For instance, Kilty in U.S. Pat. No. 4,207,210, proposes, for ethylene oxide catalysts, a silver content range of 1 to 25 weight percent and states:

"The use of larger amounts of silver is not excluded but is generally economically unattractive." (Column 4, lines 15 and 16).

Similarly, Armstrong in U.S. Pat. No. 4,342,677 states at column 4, lines 59 et seq.:

"Greater amounts of silver are unduly expensive, while lesser amounts are not desirable, since useful life and activity of the catalyst are reduced."

Armstrong broadly suggests that ethylene oxide catalysts can contain 5 to 50 weight percent silver.

Many prior workers have suggested the use of high silver loadings on ethylene oxide catalysts. For instance, Maxwell in U.S. Pat. No. 4,033,903 suggests the use of 1 to 35 weight percent silver; Hayden in U.S. Pat. No. 4,168,247 suggests 3 to 50 weight percent silver; Bhasin in U.S. Pat. No. 4,908,343 suggests 2 to 40 or more weight percent silver; Tamura in U.S. Pat. No. 4,645,754 suggests 5 to 30 weight percent silver; Sacken in U.S. Pat. No. 2,671,764 suggests 1 to 50 weight percent silver; Calcagno in U.S. Pat. No. 3,775,346 suggests 7 to 30 weight percent silver; and DeMaio in U.S. Pat. No. 3,664,970 suggests 5 to 30 weight percent silver. Yet, of these patents, only one, U.S. Pat. No. 4,908,343, provides a working example of a catalyst containing greater than 25 weight percent silver. Indeed, many workers propose a maximum silver content of 25 weight percent or less for ethylene oxide catalysts and exemplify catalysts containing only between 10 and 20 weight percent silver. Ethylene oxide catalysts manufactured on commercial bases at this time are believed to contain about 12 to 15 weight percent silver.

An insight as to why prior workers have generally tended to use silver contents in the 10 to 20 weight percent range may be perceived from a comparison of experiments using catalysts 43 and 52 of U.S. Pat. No. 4,168,247. The catalysts used in these experiments have the same carrier and promoter package but differ in silver content. Catalyst 43 contains 24 weight percent silver and catalyst 52 contains 8 weight percent silver. The oxygen conversions at 15 psia for both catalysts are identical (8 percent) and at 240 psia, the high silver content catalyst has an oxygen conversion of 3 percent while the lower silver content catalyst has an oxygen conversion of 2 percent. Under both pressure conditions, the lower silver content catalyst provides better selectivity than those exhibited using the higher silver content catalyst. This type of result would tend to confirm the observations of Kilty and Armstrong that little economic incentive exists for using high silver content catalysts.

One potential benefit of increased silver content is increased activity. Relative to efficiency gains, achieving increased activity can often readily be achieved by numerous techniques. Unfortunately, many of the techniques to increase catalyst activity, e.g., increased silver content, types and amounts of promoters and operating conditions including the presence and amounts of vapor phase modifiers such as ethylene dichloride, result in efficiency losses. Accordingly, catalysts are sought which can exhibit not only enhanced activity but also maintained or increased efficiency.

While little effort appears to be reported regarding high silver content ethylene oxide catalysts, work has been on-going in respect of carriers, or supports, for the catalysts. The carriers that have been employed are typically made of inorganic materials, generally of a mineral nature. In most cases, the preferred carrier is made of alpha-alumina, such as has been described in the patent literature: see for example, U.S. Pat. Nos. 2,294,383; 3,172,893; 3,332,887; 3,423,328 and 3,563,914.

The carriers which are employed for the manufacture of most, if not all, commercially employed ethylene oxide catalysts are produced by companies who do not produce such catalysts. As a rule, the methods of making such carriers are trade secrets of significant value to the carrier manufacturers. Consequently, the catalyst manufacturer cannot know how the carrier is made. The manufacture of a carrier for a successful ethylene oxide catalyst can involve a number of factors, such as the purity and other physical/chemical properties of raw materials used to make the carrier and the method by which the carrier is made. Description of carriers by many prior workers has thus been in terms of the chemical and/or physical properties of the catalyst.

DeMaio in U.S. Pat. No. 3,664,970 reflects the importance of physical properties of carriers in stating that:

". . . the use of a support material which is porous in nature and characterized by a limited range of pore diameters, the average pore diameter of which falls in a narrow range, can eliminate the heretofore universal need for halogenated inhibitors to temper or otherwise control the activity of the silver-containing catalysts employed in the controlled, partial oxidation of ethylene to ethylene oxide." (Column 2, lines 17 to 24).

DeMaio further postulates that:

". . . it would appear that catalyst centers exhibiting undesirable activity are minimized by the more homogeneous distribution of silver obtained by deposition thereof upon a porous support material wherein a substantial portion of the pores have diameters which fall within a limited range and wherein the average pore diameter falls within a narrow range." (Column 2, line 50 to 56). "The invention contemplates that the 'average pore diameter' will be of a size such that neither too low [nor] too high a diffusion rate is encountered in practice." (Column 2, line 74 to column 3, line 1).

DeMaio proposes that an average pore diameter of 4 to 10 microns is optimum without the need to employ a halogenated inhibitor. The patentee states that at least 90 percent of the pores have diameters in the range of 1 to 30 microns. No information is presented by the patentee on surface area of the carrier, and the reported porosities of the exemplified carriers ranged up to 56 percent.

Jin, et al., in European Patent Application 327,356 state:

"In order to increase the activity of the catalysts, the sufficient specific surface area of silver particles must be afforded. Therefore, the catalyst carriers are required to have enough specific surface area. However, oversized specific surface area will make the transfer of the reaction heat difficult, aggravate side reaction and decrease the selectivity of the catalysts. In order to offer the catalysts a high selectivity, an ideal pore structure which matches the surface of the catalyst is required so that suitable conditions for heat and mass transfer can be attained and side reaction can be suppressed. Since the reaction takes place under nearly diffusion-controlling conditions, searching for carriers with an optimum matching between pore structure and specific surface area has become an important subject in developing silver catalysts with a high selectivity." (page 2, lines 7 to 15)

Jin, et al., propose carrier for silver, epoxidation catalysts which have a specific surface area of 0.2 to 2 $m^2/g$, preferably 0.8 to 1.3 $m^2/g$; a total pore volume greater than 0.5 milliliters per gram, preferably 0.5 to 0.7 milliliters per gram; and pores of a pore radius of less than 30 microns comprise 75 to 90 percent of the total volume and those greater than 30 microns, between 25 and 10 percent of the total volume. In the examples, the predominant distribution of the pores in the carriers is in the 0.5 to 5 micron range. Jin, et al., state that the silver content is between 1 to 25 weight percent, but the examples use conventional silver loadings.

Hayden, et al., in U.S. Pat. No. 4,168,247 proposes the use of bimodal carrier for silver, epoxidation catalysts. The smaller pores are preferably to account for at least 70 percent of the total pore volume and have a mean pore diameter of 0.1 to 4 microns and the larger pores are to have a mean pore diameter of 25 to 500 microns. The apparent porosity is at least 20 percent, for example, 30 to 80 percent. The patentees propose that the amount of promoters present be in relation to the surface area of the support. Although silver contents ranging from 3 to 50% and more, preferably 3 to 30%, are suggested, no guidance is presented by the patentees as to the manner for effective utilization of the silver other than it should be in the form of discrete particles having equivalent diameters of less than 10000 Angstoms. As stated above, the higher silver content catalysts disclosed by Hayden, et al., provide no demonstrable benefit over lower silver content catalysts.

Cognion, et al., in U.S. Pat. No. 4,242,235 also disclose the use of bimodal carriers for silver, epoxidation catalysts. The patentees state:

"... the coexistence of two ranges of porosity consisting of pores of different diameters was favorable to the selectivity of ethylene oxide." (Column 2, line 20 to 23).

The ranges are 1 to 5 microns and 60 to 200 microns. Each of these ranges preferably represents 35 to 65 percent of the total porosity. Other features of the support are said to be a surface area of less than 10 square meters per gram ($m^2/g$) advantageously, between 0.1 and 1 $m^2/g$ and a porosity of up to 60 percent, preferably between 20 and 50 percent. The surface area of the carriers in the working examples is no more than 0.3 $m^2/g$ and the maximum porosity is 0.34 cubic centimeters per gram.

Boehning, et al., in U.S. Pat. No. 4,829,043 disclose ethylene oxide catalysts in which carriers of certain physical properties are used to provide a silver density in the reactor of not less than 110 kilograms per cubic meter. The carrier has a surface area of 0.4 to 0.8 $m^2/g$ and a pore volume of not less than 0.45 milliliter per gram. The patentees assert that the carrier is important to the activity of the catalysts and state that if the carrier is monomodal, the mean pore diameter is from 1 to 5 microns; and if bimodal, 50 percent of the total pore volume is of pores having a mean diameter of 10 to 40 microns and the smaller pores have a diameter of 0.5 to 2 microns.

Saffer in U.S. Pat. No. 3,207,700 discloses a composite support for silver, epoxidation catalysts. The outer margin is a porous material and a dense, substantially non-porous material forms the core. The outer margin has a porosity of 15 to 40 percent. The exemplified catalyst support has a surface area of the outer margin of less than 1 $m^2/g$, a porosity of 28 percent and about 80 percent of the pore volume is constituted by pores in the range of 1 to 3 microns. The composite carrier is said to provide substantially enhanced activity when formulated into a catalyst as compared to that of a catalyst formed from a homogeneous, high porosity support.

Numerous workers have disclosed broad ranges for carrier physical properties. Exemplary of such disclosures is Maxwell, in U.S. Pat. No. 4,033,903 who characterizes suitable carriers as having a surface area below 10 $m^2/g$ and preferably below 2 $m^2/g$. The carriers are said to have an apparent porosity of greater than 20 percent. See also, for instance, Lauritzen, U.S. Pat. No. 4,761,394. Although broad ranges are presented, the actually exemplified carriers are often quite limited in scope. Lauritzen does exemplify one carrier, albeit a carrier containing only 70 to 75 weight percent alumina, having greater than 0.6 $m^2/g$ surface area.

U.S. Pat. Nos. 4,368,144; 4,376,209; 4,389,338; 4,645,754; 4,769,358; 4,812,437 and 4,831,162 do, however, exemplify carriers for ethylene oxide catalysts which have higher surface areas, i.e., 0.7 $m^2/g$ and above.

Although the foregoing documents indicate that work has been devoted to the development of carrier for silver, epoxidation catalysts, little, or no, guidance is given by these workers regarding the effect of carrier physical properties on the silver content of the catalysts. Often lower surface area carriers e.g., 0.3 to 0.6 $m^2/g$, are employed, within the field of catalysts which contain conventional amounts of silver.

SUMMARY OF THE INVENTION

By the present invention silver-containing, supported alkylene oxide catalysts suitable for the epoxidation of alkene to alkylene oxide are provided having enhanced activity and/or stability. In accordance with this invention, silver epoxidation catalysts are provided in which advantages of high silver content can be realized. The catalysts and processes of this invention use, in combination with higher silver content (i.e., at least about 25 weight percent silver), a high surface area, high porosity carrier.

In some more preferred aspects of the invention, the carrier is characterized as having a median pore diameter of between about 1 and 25, preferably about 3 to 20, microns; between about 10 to 25 volume percent of the pores (based on the total volume of pores greater than 0.1 micron) having a pore diameter of between about 0.5 and 1 micron; at least about 10 volume percent of the pores have a pore diameter between about 1 and 10 microns; and at least about 20 volume percent of the pores having a pore diameter between about 10 and 100, preferably between 10 and 30, microns. The water pore volume is often greater than about 0.5, say, about 0.5 to 2.0, milliliters per gram. Advantageously, with all else the same but pore distribution, high silver catalysts of this invention can exhibit enhanced activity without sacrifice in efficiency as compared to catalysts not having such high surface areas and pore distributions.

The catalysts contain a high concentration of silver, generally at least about 25 or 30 percent by weight, based on the total weight of the catalyst, more generally in the range of from about 25 or 30 percent to about 60 percent by weight and more preferably in the range of from about 25 or 35 percent by weight to about 45 percent by weight of silver. On a volume basis (bulk density), the amount of silver present in the catalysts of the present invention is often greater than about 0.4 gram of silver per cubic centimeter of finished catalyst, generally in the range of from about 0.4 to about 2.0 g/cc (grams per cubic centimeter), and more preferably in the range of from about 0.54 to about 0.91 g/cc. The bulk density of a catalyst is typically much higher than packed density in, e.g., a tubular reactor such as commercially used for the production of ethylene oxide. The silver density per cubic centimeter of a tubular reactor packed with catalyst in accordance with this invention is often at least about 0.2 g/cc, e.g., about 0.2 to 0.9 g/cc.

By containing this high level of silver, the catalysts of this invention are often able to increase the activity of the catalyst, as determined under Standard Ethylene Oxide Process Conditions (herein defined), by at least about 5° C., preferably at least about 10° C., or more, as compared to a similar catalyst not having the same support and/or high silver concentration.

In the preferred aspects of this invention, the selectivity, or efficiency, of the catalysts to produce alkylene oxide is maintained, or preferably enhanced, with the increased silver content of the catalyst. Often, the efficiency increase over a catalyst otherwise the same but containing between about 12 to 15 weight percent silver, under Standard Ethylene Oxide Process Conditions to produce 2.0 percent delta ethylene oxide, is at least about 1, preferably about 1 or 2 to 10, say, about 2 to 7, efficiency percentage points. Surprisingly, the advantageous carriers used in this invention are often less desirable than lower surface area carriers when conventional silver contents are used.

DETAILED DISCUSSION OF THE INVENTION

Alkylene oxides made using the catalysts of this invention are characterized by the structural formula

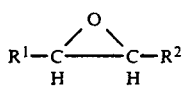

wherein $R^1$ and $R^2$ are lower alkyl, e.g., methyl or ethyl or, preferably, hydrogen. Most preferably, the alkylene oxide is ethylene oxide. The alkylene oxides are made from the corresponding alkene, i.e., $R^1HC=CHR^2$. For purposes of ease of understanding, the following discussion will be made with reference to ethylene oxide and ethylene.

The catalysts of this invention are characterized by containing silver in an amount of greater than about 0.2 of silver per cubic centimeter of finished catalyst (packed in a tubular reactor), which silver is supported on a carrier having a specific surface area of greater than about 0.7 m²/g and a pore volume of at least about 0.5 cc/g. The carriers have a water pore volume as measured by conventional water absorption techniques of at least about 0.5 cc/g, generally in the range of from about 0.5 to about 2.0 cc/g, preferably greater than about 0.55 cc/g, and most preferably from about 0.6 to about 0.8 cc/g.

In conjunction with such high silver concentration, the carriers of the catalysts of the present invention have a high surface area and a high pore volume. Generally, suitable carriers have a specific surface area as measured by the B.E.T. method (herein defined) of greater than about 0.7 m²/g, generally in the range of from about 0.7 m²/g to about 10 m²/g. Preferably, the specific surface area of the carrier as measured by the B.E.T. method is preferably in the range of from about 0.8 to about 1.6 m²/g, or more. The B.E.T. method for determining specific surface area is described in detail in Brunauer, S., Emmet, P. and Teller, E. *J. Am. Chem. Soc.*, 60, 309–16 (1938). Preferably, these carriers also have a water pore volume as measured by conventional water absorption techniques of greater than about 0.55 cc/g, and most preferably from about 0.6 to about 0.8 cc/g.

The support or carrier employed in these catalysts may be selected from the large number of porous refractory catalyst carriers or support materials which are considered relatively inert in the presence of the alkene epoxidation feeds, products and reaction conditions. Carriers may be composed, for example, of alpha-alumina, silicon carbide, silicon dioxide, zirconia, magnesia and various clays. The preferred carriers are alpha-alumina particles often bonded together by a bonding agent and have a very high purity, i.e., at least 98 wt. % alpha-alumina, any remaining components being other phases of alumina, silica, alkali metal oxides (e.g., sodium oxide) and trace amounts of other metal-containing and/or non-metal-containing additives or impurities. A wide variety of such carriers are commercially available. Alumina carriers are manufactured by United Catalysts, Inc., Louisville, Ky., and the Norton Company, Akron, Ohio.

Median pore diameters for the above-described carriers range from about 1 to 50 microns, a more preferred range being from about 1 to 25 microns, and most preferred in the range of from about 3 to about 20 microns. The carriers may have monomodal, bimodal or multimodal pore distributions.

Often, advantageous carriers have pore distributions as set forth in Table A.

TABLE A

| Pore Diameters, microns | Percent of Pores, Vol. % | |
|---|---|---|
| | Desired | Preferred |
| less than 0.1 | <20 | 0 to 5 |
| 0.1 to 0.5 | 5 to 30 | 5 to 20 |
| 0.5 to 1.0 | 7 to 30 | 10 to 25 |
| 1.0 to 10 | >10 | 10 to 40 |
| 10 to 100 | >20 | 30 to 55 |
| 100 and greater | 4 to 20 | 6 to 20 |

The surface acidity of the carrier, as determined by irreversible ammonia sorption at 100° C., is often less than about 2, preferably less than about 1.5, and often between about 0.05 to 1.0, micromoles per gram of carrier.

In one aspect of the invention, the carrier is composed of a particulate matrix in which at least about 50 percent of the total number of carrier particles having a particle size greater than about 0.1 micrometer have at least one substantially flat major surface which may be characterized as having a lamellate or platelet-type morphology. Some of the particles have two, or sometimes more, flat surfaces. The major dimension of a substantial portion of the particles having platelet-type morphology is less than about 50 microns, preferably less than about 20 microns. When alpha-alumina is utilized as the support material, the platelet-type particles frequently have a morphology which approximates the shape of hexagonal plates. A complete discussion of such platelet-type carriers is set forth in U.S. patent application Ser. No. 765,207, filed Aug. 13, 1985, herein incorporated by reference.

In another aspect of the invention, the carrier, whether having a platelet-type morphology or not, contains a fluorine-containing substance. Carriers containing fluorine-containing substances appear to help improve the performance, particularly the stability, of the catalyst. The fluorine-containing material is generally introduced into the carrier as it is being prepared, and is preferably somewhat volatile or can be volatilized under roasting conditions. Applicable fluorine-containing materials include, but are not limited to, aluminum trifluoride, ammonium fluoride, hydrofluoric acid, and dichlorodifluoromethane. A complete discussion of carriers containing such fluorine-containing substances is set forth in U.S. patent application Ser. No. 765,068, filed Aug. 13, 1985, herein incorporated by reference.

As stated above, carrier manufacture is typically maintained as a trade secret by carrier manufacturers. However, insights into processes for making carriers and affecting the distribution of pore sizes in carriers are provided by, for instance, Trimm, et al., "The Control of Pore Size in Alumina Catalyst Supports: A Review", Appl. Catal., Vol. 21, 215 (1986); Young, et al., U.S. Pat. No. 4,575,494; Belon, et al., U.S. Pat. No. 3,172,866; Lin, et al. U.S. Pat. No. 4,356,113; Tamm, U.S. Pat. No. 4,082,697; Pearson, et al., U.S. Pat. No. 4,001,144; Carithers, U.S. Pat. No. 3,856,708; Kiovsky, et al., U.S. Pat. No. 3,850,849 and Robayashi et al., U.S. Pat. No. 3,526,602, all herein incorporated by reference.

Regardless of the character of the support or carrier used, it is preferably shaped into particles, chunks, pieces, pellets, rings, spheres, cylinders, wagon wheels, and the like of a size suitable for employment in fixed bed reactors. Conventional commercial fixed bed ethylene oxide reactors are typically in the form of a plurality of parallel elongated tubes (in a suitable shell) approximately 0.7 to 2.7 inches O.D. and 0.5 to 2.5 inches I.D. and 15-45 feet long filled with catalyst. In such reactors, it is desirable to employ a support formed into a rounded shape, such as, for example, spheres, cylinders, pellets, rings, tablets and the like, having diameters from about 0.1 inch to about 0.8 inch.

As with any supported catalyst, the optimal performance will depend upon optimizing the carrier in terms of its chemical composition (including impurities), surface area, porosity and pore volume.

Although the catalysts can be used under widely varying process conditions, for purposes of determining activity and stability, a standard set of process conditions can be used.

The STANDARD ETHYLENE OXIDE PROCESS CONDITIONS (ABBR. "CONDITIONS") for characterizing the catalysts of this invention involve the use of a standard backmixed autoclave with full gas recycle including carbon dioxide. The CONDITIONS may be operated with some variation in ethylene, oxygen and gas phase inhibitor feed. Two cases are illustrated: air process conditions, which simulates in the backmixed reactor the typical conditions employed in commercial air-type ethylene oxide processes where air is used to supply the molecular oxygen and the oxygen process conditions, which simulates in the backmixed reactor the typical conditions in commercial oxygen-type ethylene oxide processes where molecular oxygen, as such, is employed. Each case provides a different efficiency but it is the rule for practically all cases that air as the oxygen feed, using lower amounts of oxygen and ethylene, will yield an efficiency to ethylene oxide which is about 2 to 5 percentage points lower than that when molecular oxygen is employed as oxygen feed. The CONDITIONS employ the well known backmixed bottom-agitated "Magnedrive" autoclaves described in FIG. 2 of the paper by J. M. Berty entitled "Reactor for Vapor Phase-Catalytic Studies", in *Chemical Engineering Progress*, Vol. 70, No. 5, pages 78-84, 1974. The CONDITIONS employ 2.0 mole % ethylene oxide in the outlet gas of the reactor under the following standard inlet conditions:

| Component | Air process Conditions, Mole % | Oxygen process Conditions, Mole % |
|---|---|---|
| Oxygen | 6.0 | 8.0 |
| Ethylene | 8.0 | 30 |
| Ethane | 0.5 | 0.5 |
| Carbon Dioxide | 6.5 | 6.5 |
| Nitrogen | Balance of Gas | Balance of Gas |
| Parts per million ethyl chloride (or one-half such amount when ethylene dichloride is used) | Optimum for Efficiency | Optimum for Efficiency |

The pressure is maintained constant at 275 psig and the total outlet flow is maintained at 22.6 SCFH. SCFH refers to cubic feet per hour at standard temperature and pressure, namely, 0° C. and one atmosphere. The outlet ethylene oxide concentration is maintained at 2.0% by adjusting the reaction temperature. Thus temperature (° C.) and catalyst efficiency are obtained as the responses describing the catalyst performance.

The catalyst test procedure used in the CONDITIONS involves the following steps:

1. 80 cc of catalyst is charged to the backmixed autoclave. The volume of catalyst is measured in a 1 inch I.D. graduated cylinder after tapping the cylinder several times to thoroughly pack the catalyst. The volume of catalyst is alternatively calculated from the packing density of the carrier and the amount of silver and additives. The weight of the catalyst is noted.

2. The backmixed autoclave is heated to about reaction temperature in a nitrogen flow of 20 SCFH with the fan operating at 1500 rpm. The nitrogen flow is then discontinued and the above-described feed stream is introduced into the reactor. The total gas outlet flow is adjusted to 22.6 SCFH. The temperature is adjusted over the next few hours so that the ethylene oxide concentration in the outlet gas is approximately 2.0%.

3. The outlet oxide concentration is monitored over the next 4-6 days to make certain that the catalyst has reached its peak steady state performance. The temperature is periodically adjusted to achieve 2% outlet oxide. The selectivity of the catalyst to ethylene oxide and the temperature are thus obtained.

The standard deviation of a single test result reporting catalyst efficiency in accordance with the procedure described above is about 0.7% efficiency units. The standard deviation of a single test result reporting catalyst activity in accordance with the procedure described above is about 1.2° C. The standard deviation, of course, will depend upon the quality of the equipment and precision of the techniques used in conducting the tests, and thus will vary. The test results reported herein are believed to be within the standard deviation set forth above. The running of a multiplicity of tests will reduce the standard deviation by the square root of the number of tests.

In determining the increase in efficiency, the process and catalyst should be under steady state conditions, and can often be ascertained promptly upon steady state conditions being achieved.

As with any catalyst for making ethylene oxide which provides optimum performance, a correlation exists among many factors. Factors frequently considered include:

(i) the nature of the support;
(ii) the amount of silver on or in the support;

(iii) the components (including promoters) and amounts thereof in or on the support;
(iv) the impurities or contaminants provided with the silver, support or other components;
(v) the procedure to make the catalyst; and
(vi) the conditions under which the catalyst is used to produce ethylene oxide.

The catalysts of this invention preferably contain at least one or more promoters or modifiers to enhance the performance of the catalyst, e.g., to enhance efficiency or reduce the burning of ethylene oxide or affect activity. These promoters or modifiers are generally provided as chemical compounds.

As used herein, the term "compound" refers to the combination of a particular element with one or more different elements by surface and/or chemical bonding, such as ionic and/or covalent and/or coordinate bonding. The term "ionic" or "ion" refers to an electrically charged chemical moiety; "cationic" or "cation" being positive and "anionic" or "anion" being negative. The term "oxyanionic" or "oxyanion" refers to a negatively charged moiety containing at least one oxygen atom in combination with another element. An oxyanion is thus an oxygen-containing anion. It is understood that ions do not exist in vacuo, but are found in combination with charge-balancing counter ions.

The catalyst preferably contains at least one or more promoters in an amount sufficient to enhance the efficiency and/or activity of the catalyst. (References to the Periodic Table herein shall be to that as published by the Chemical Rubber Company, Cleveland, Ohio, in *CRC Handbook of Chemistry and Physics*, 46th Edition, inside back cover.) The preferred promoters include the halides, e.g., fluorides and chlorides, and the oxyanions of the elements other than oxygen having an atomic number of 5 to 83 of Groups 3b to 7b and 3a to 7a of the Periodic Table. Most preferably, the promoters are one or more of the oxyanions of nitrogen, sulfur, manganese, tantalum, molybdenum, tungsten and rhenium.

For the sake of ease of understanding, the promoters will be referred to in terms of cation promoters, e.g., alkali and alkaline earth metals, and anion promoters. Compounds such as alkali metal oxide or $MoO_3$, while not being ionic, may convert to ionic compounds, e.g., during catalyst preparation or in use. Whether or not such a conversion occurs, they will be referred to herein in terms of cation and anion species, e.g., alkali metal or molybdate.

Frequently, the catalyst contains alkali metal and/or alkaline earth metal as cationic promoter. Exemplary of the alkali metal and/or alkaline earth metals are lithium, sodium, potassium, rubidium, cesium, beryllium, magnesium, calcium, strontium and barium. Other cationic promoters include Group 3b metal ions including lanthanide series metals. In some instances, the promoter comprises a mixture of cations, e.g., cesium and at least one other alkali metal, to obtain a synergistic efficiency enhancement as described in British Patent No. 2,043,481, herein incorporated by reference.

In many instances, the catalyst preferably comprises salt(s) of oxyanion of an element (other than oxygen) having an atomic number of 5 to 83 and being from groups 3b to 7b or groups 3a to 7a, inclusive, of the Periodic Table In some instances, it has been found beneficial to add more anion than is required to associate with the total alkali metal and alkaline earth metal being provided to the catalyst. The reason why such additional anion is beneficial in these situations is not known. The additional anion may be added in the form of an acid, an ammonium salt, an amine salt, etc., or a portion of the alkali metal and/or alkaline earth metal may be added as an acid salt, e.g., cesium hydrogen sulfate.

The concentration of the salt(s) (including any alkali metal and alkaline earth metal salts) in the finished catalyst is not narrowly critical and may vary over a wide range. The optimum cesium salt and other salt concentration for a particular catalyst will be dependent upon performance characteristics, such as catalyst efficiency, rate of catalyst aging and reaction temperature.

The concentration of salt (based on the weight of cation, e.g., cesium) in the finished catalyst may vary from about 0.0005 to 1.0 weight percent, preferably from about 0.005 to 0.1 weight percent. The preferred amount of cation promoter deposited on or present on the surface of the carrier or catalyst generally lies between about 10 and about 4000, preferably about 15 and about 3000 and more preferably between about 20 and about 2500 ppm by weight of cation calculated on the total carrier material. Amounts between about 50 and about 2000 ppm are frequently most preferable. When cesium is used in mixture with other cations, the ratio of cesium salt to any other alkali metal and alkaline earth metal salt(s), if used, to achieve desired performance is not narrowly critical and may vary over a wide range. The ratio of cesium salt to the other salt(s) may vary from about 0.0001:1 to 10,000:1, preferably from about 0.001:1 to 1,000:1. Preferably, cesium comprises at least about 10, more preferably, about 20 to 100, percent (weight) of the total added alkali metal and alkaline earth metal in the finished catalyst.

The types of anion promoters or modifiers suitable for use in the catalysts of this invention comprise, by way of example only, oxyanions such as sulfate, $SO_4^{-2}$, phosphates, e.g., $PO_4^{-3}$, titanates, e g., $TiO_3^{-2}$, tantalates, e.g., $Ta_2O_6^{-2}$, molybdates, e.g., $MoO_4^{-2}$, vanadates, e.g., $V_2O_4^{-2}$, chromates, e.g., $CrO_4^{-2}$, zirconates, e.g., $ZrO_3^{-2}$, polyphosphates, manganates, nitrates, chlorates, bromates, borates, silicates, carbonates, tungstates, thiosulfates, cerates and the like. The halide ions may also be present as anions and include fluoride, chloride, bromide and iodide. Other salts such as sulfides may find application.

It is well recognized that many anions have complex chemistries and may exist in one or more forms, e.g., orthovanadate and metavanadate; and the various molybdate oxyanions such as $MoO_4^{-2}$, and $Mo_7O_{24}^{-6}$ and $Mo_2O_7^{-2}$. The oxyanions may also include mixed metal-containing oxyanions including polyoxyanion structures. For instance, manganese and molybdenum can form a mixed metal oxyanion. Similarly, other metals, whether provided in anionic, cationic, elemental or covalent form may enter into anionic structures.

While an oxyanion, or a precursor to an oxyanion, may be used in solutions impregnating a carrier, it is possible that during the conditions of preparation of the catalyst and/or during use, the particular oxyanion or precursor initially present may be converted to another form. Indeed, the element may be converted to a cationic or covalent form. Preferably, the element is associated with oxygen, i.e., is an oxyanion, a covalent oxide or has an oxygen-containing anion. In many instances, analytical techniques may not be sufficient to precisely identify the species present. The invention is not intended to be limited by the exact species that may ultimately exist on the catalyst during use but rather reference herein to oxyanions is intended to provide guidance to understanding and practicing the invention.

A particularly preferred anion promoter includes the sulfates and oxyanions of rhenium, molybdenum, tungsten and/or chromium. Examples of anions of sulfur that can be suitably applied include sulfate, sulfite, bisulfite, bisulfate, sulfonate, persulfate, thiosulfate, dithionate, dithionite, halosulfate, e.g., fluorosulfate, etc. Preferred compounds to be applied are ammonium sulfate and the alkali metal sulfates. Examples of anions of molybdenum, tungsten and chromium that can be suitably applied include molybdate, dimolybdate, paramolybdate, other iso- and heteropolymolybdates, etc.; tungstate, paratungstate, metatungstate, other iso- and hetero- polytungstates, etc.; and chromate, dichromate, chromite, halochromate, etc. Preferred are sulfates, molybdates, tungstates and chromates.

When the catalyst comprises rhenium, the rhenium component can be provided in various forms, e.g., as the metal, as a covalent compound, as a cation or as an anion. The rhenium species that provides the enhanced efficiency and/or activity is not certain and may be the component added or that generated either during preparation of the catalyst or during use as a catalyst. Examples of rhenium compounds include the rhenium salts such as rhenium halides, the rhenium oxyhalides, the rhenates, the perrhenates, the oxides and the acids of rhenium. However, the alkali metal perrhenates, alkaline earth metal perrhenates, silver perrhenates, other perrhenates and rhenium heptoxide can also be suitably utilized. Rhenium heptoxide, $Re_2O_7$, when dissolved in water, hydrolyzes to perrhenic acid, $HReO_4$, or hydrogen perrhenate. Thus, for purposes of this specification, rhenium heptoxide can be considered to be a perrhenate, i.e., $ReO_4$. Similar chemistries can be exhibited by other metals such as molybdenum and tungsten.

Another class of promoters includes manganese components. In many instances, manganese components can enhance the activity, efficiency and/or stability of catalysts. The manganese species that provides the enhanced activity, efficiency and/or stability is not certain and may be the component added or that generated either during catalyst preparation or during use as a catalyst. Manganese components include, but are not limited to, manganese acetate, manganese ammonium sulfate, manganese citrate, manganese dithionate, manganese oxalate, manganous nitrate, manganous sulfate, and manganate anion, e.g., permanganate anion, manganate anion, and the like.

The amount of anion promoter may vary widely, e.g., from about 0.0005 to 2 weight percent, preferably from about 0.001 to 0.5 weight percent based on the total weight of the catalyst. When used, the rhenium component is often provided in an amount of at least about 1, say, at least about 5, e.g., about 10 to 2000, often between 20 and 1000, ppmw calculated as the weight of rhenium based on the total weight of the catalyst.

The catalysts of this invention may be of the type comprising at least one efficiency-enhancing salt of a member of a redox-half reaction pair which are intended to be employed in epoxidation processes in which at least one efficiency-enhancing gaseous member of a redox-half reaction pair is present (described hereinbelow). The term "redox-half reaction" is defined herein to mean half-reactions like those found in equations presented in tables of standard reduction or oxidation potentials, also known as standard or single electrode potentials, of the type found in, for instance, "Handbook of Chemistry", N. A. Lange, Editor, McGraw-Hill Book Company, Inc., pages 1213–1218 (1961) or "CRC Handbook of Chemistry and Physics", 65th Edition, CRC Press, Inc., Boca Raton, Fla., pages D155–162 (1984). The term "redox-half reactions pair" refers to the pairs of atoms, molecules or ions or mixtures thereof which undergo oxidation or reduction in such half-reaction equations. Such terms as redox-half reaction pairs are used herein to include those members of the class of substance which provide the desired performance enhancement, rather than a mechanism of the chemistry occurring. Preferably, such compounds, when associated with the catalyst as salts of members of a half reaction pair, are salts in which the anions are oxyanions, preferably an oxyanion of a polyvalent atom; that is, the atom of the anion to which oxygen is bonded is capable of existing, when bonded to a dissimilar atom, in different valence states. Potassium is the preferred cation, although sodium, rubidium and cesium may also be operable, and the preferred anions are nitrate, nitrite and other anions capable of undergoing displacement or other chemical reaction and forming nitrate anions under epoxidation conditions. Preferred salts include $KNO_3$ and $KNO_2$, with $KNO_3$ being most preferred.

The salt of a member of a redox-half reaction pair is added in an amount sufficient to enhance the efficiency of the epoxidation reaction. The precise amount will vary depending upon such variables as the gaseous efficiency-enhancing member of a redox-half reaction used and concentration thereof, the concentration of other components in the gas phase, the amount of silver contained in the catalyst, the surface area of the support, the process conditions, e.g., space velocity and temperature, and morphology of support. Generally, however, a suitable range of concentration of the added efficiency-enhancing salt, calculated as cation, is about 0.01 to about 5 percent, preferably about 0.02 to about 3 percent, by weight, based on the total weight of the catalyst. Most preferably the salt is added in an amount of about 0.03 to about 2 weight percent.

In any event, the cation and/or anion promoters are provided in a promoting amount. As used herein the term "promoting amount" of a certain component of a catalyst refers to an amount of that component that works effectively to provide an improvement in one or more of the catalytic properties of that catalyst when compared to a catalyst not containing said component. Examples of catalytic properties include, inter alia, operability (resistance to run-away), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement shows up in the activity rather than the selectivity and an operator of an ethylene oxide plant will intentionally change the operating conditions in order to take advantage of certain catalytic properties even at the expense of other catalytic properties in order to maximize profits by taking into account feedstock costs, energy costs, by-product removal costs and the like.

The promoting effect provided by the promoters can be affected by a number of variables such as for example, reaction conditions, catalyst preparative techniques, surface area and pore structure and surface chemical properties of the support, the silver and co-promoter content of the catalyst, the presence of other cations and anions present on the catalyst. The presence of other activators, stabilizers, promoters, enhancers or other catalyst improvers can also affect the promoting effects.

A variety of procedures may be employed for preparing catalysts in accordance with the present invention. It is desirable that the silver and the at least one or more promoters be relatively uniformly dispersed on the catalyst. The preferred procedure comprises: (1) impregnating a porous catalyst carrier with a solution comprising a solvent or solubilizing agent, silver complex and the aforementioned anion and/or cation promoters upon the carrier, and (2) thereafter treating the impregnated support to convert the silver salt to silver metal and effect deposition of silver and the anion and/or cation promoters onto the exterior and interior surfaces of the support. For sake of repeatability, in the use and reuse of impregnating solutions the carrier should preferably not contain undue amounts of ions which are soluble in the impregnating solution and/or exchangeable with the promoter supplied to the catalyst, either in the preparation or use of the catalyst, so as to upset the amount of promoter which provides the desired catalyst enhancement. If the carrier contains such ions, the ions should generally be removed by standard chemical techniques such as leaching, otherwise they must be taken into account during the catalyst preparation. Silver and promoter depositions are generally accomplished by heating the carrier at elevated temperatures to evaporate the liquid within the support and effect deposition of the silver and promoters onto the interior and exterior carrier surfaces. Impregnation of the carrier is the preferred technique for silver deposition because it utilizes silver more efficiently than coating procedures, the latter being generally unable to effect substantial silver deposition onto the interior surface of the carrier. In addition, coated catalysts are more susceptible to silver loss by mechanical abrasion.

The silver solution used to impregnate the carrier is comprised of a silver compound in a solvent or complexing/solubilizing agent such as the silver solutions disclosed in the art. The particular silver compound employed may be chosen, for example, from among silver complexes, nitrate, silver oxide or silver carboxylates, such as silver acetate, oxalate, citrate, phthalate, lactate, propionate, butyrate and higher fatty acid salts. Desirably, silver oxide complexed with amines is the preferred form of silver in the practice of the invention.

A wide variety of solvents or complexing/solubilizing agents may be employed to solubilize silver to the desired concentration in the impregnating medium. Among those disclosed as being suitable for this purpose are lactic acid (U.S. Pat. Nos. 2,477,436 to Aries, and 3,501,417 to DeMaio); ammonia (U.S. Pat. No. 2,463,228 to West, et al.); alcohols, such as ethylene glycol (U.S. Pat. Nos. 2,825,701 to Endler, et al., and 3,563,914 to Wattimina); and amines and aqueous mixtures of amines (U.S. Pat. Nos. 2,459,896 to Schwarz; 3,563,914 to Wattimina; 3,215,750 to Benisi; 3,702,259 to Nielsen; and 4,097,414, 4,374,260 and 4,321,206 to Cavitt).

Generally, the amount of silver compound that is dissolved in the silver impregnation solution is more than that ultimately provided on the finished catalysts per impregnation. For example, $Ag_2O$ can be dissolved in a solution of oxalic acid and ethylenediamine to an extent of approximately 30% by weight. Vacuum impregnation of such a solution onto an alpha alumina support of approximately 0.7 cc/g porosity results in a catalyst containing approximately 25% by weight of silver based on the entire weight of the catalyst. Accordingly, in order to obtain catalysts having a silver loading of greater than about 25 or 30%, and more, it is necessary to subject the carrier to at least two or more sequential impregnations of silver, with or without promoters, until the desired amount of silver is deposited on the carrier. Usually, two or more impregnations are used to make the catalysts of this invention. In some instances, the concentration of the silver salt is higher in the latter impregnation solutions than in the first. For example, if a total silver concentration of say about 30% were desired in the catalyst, a low amount of silver of about 10% by weight would be deposited on the carrier as a result of the first impregnation followed by a second silver impregnation depositing the remaining 20% by weight. In other instances, approximately equal amounts of silver are deposited during each impregnation step. Often, to effect the equal deposition in each impregnation step, the silver concentration in the subsequent impregnation solutions may need to be greater than that in the initial impregnation solutions. In further instances, a greater amount of silver is deposited on the carrier in the initial impregnation than that deposited in subsequent impregnations. Each of the impregnations may be followed by roasting or other procedure to render the silver insoluble.

The sequence of impregnating or depositing the surfaces of the carrier with silver and promoters is optional. Thus, impregnation and deposition of silver and salts may be effected coincidentally or sequentially, i.e., the promoters may be deposited prior to, during, or subsequent to silver addition to the carrier. The promoters may be deposited together or sequentially. For example, one or more of the salts may be deposited first followed by the coincidental or sequential deposition of silver and additional or other salts.

Impregnation of the catalyst carrier may be effected using one or more solutions containing silver and promoters in accordance with well-known procedures for coincidental or sequential depositions. For coincidental deposition, following impregnation the impregnated carrier is heat or chemically treated to reduce the silver compound to silver metal and deposit the salts onto the catalyst surfaces.

For sequential deposition, the carrier is initially impregnated with silver or promoter (depending upon the sequence employed) and then heat or chemically treated as described above. This is followed by a second impregnation step and a corresponding heat or chemical treatment to produce the finished catalyst containing silver and promoters.

In a preferred embodiment of the present invention, the one or more promoters are added coincidentally with the silver. Even more preferably, the one or more promoters are added to the catalyst in the very last silver impregnation step. These embodiments have been found to help increase the efficiency and activity of the resulting catalysts, particularly when using nitrate promoted catalysts.

In making the catalysts of this invention, some promoters such as some alkali and alkaline earth metal salts have such high melting temperatures that when deposited on the support with silver compound, and subjected to heating to convert the silver compound to silver metal, the salts may remain essentially unchanged. Of course, it is realized that alkali metal and alkaline earth metal salts having an unstable anion oxidation state will change to a stable oxidation state or states, e.g., sulfites to sulfates. When, for instance, the alkali metal or alkaline earth metal is deposited as the hydroxide or carbonate, it may be transformed in the presence of amines, which may be used in the impregnation of the catalyst, to a different salt form (i.e., nitrate) during the heating (roasting) step depending on the roast conditions. If the deposited material is sufficiently volatile, some loss may occur during roasting.

Following each impregnation of the catalyst carrier with silver and promoter, the impregnated carrier particles are separated from any remaining non-absorbed solution. This is conveniently accomplished by draining the excess impregnating medium or, alternatively, by using separation techniques, such as filtration or centrifugation. The impregnated carrier is then generally heat treated (e.g., roasted) to effect decomposition and reduction of the silver metal compound (complexes in most cases) to metallic silver and the deposition of alkali metal and alkaline earth metal salts. Such roasting may be carried out at a temperature of from about 100° C. to 900° C., preferably from 200° to 700° C., for a period of time sufficient to convert substantially all of the silver salt to silver metal. In general, the higher the temperature, the shorter the required reduction period. For example, at a temperature of from about 400° C. to 900° C., reduction may be accomplished in about 1 to 5 minutes. Although a wide range of heating periods have been suggested in the art to thermally treat the impregnated support, (e.g., U.S. Pat. No. 3,563,914 suggests heating for less than 300 seconds to dry, but not roast to reduce, the catalyst; U.S. Pat. No. 3,702,259 discloses heating from 2 to 8 hours at a temperature of from 100° C. to 375° C. to reduce the silver salt in the catalyst; and U.S. Pat. No. 3,962,136 suggests ½ to 8 hours for the same temperature range), it is only important that the reduction time be correlated with temperature such that substantially complete reduction of the silver salt to metal is accomplished. A continuous or step-wise heating program is desirably used for this purpose. Continuous roasting of the catalyst for a short period of time, such as for not longer than ½ hour is preferred and can be effectively done in making the catalysts of this invention. When more than one roasting step is used, it is not necessary that the roasting conditions be the same in each roasting step.

Heat treatment is preferably carried out in air, but a nitrogen or carbon dioxide atmosphere may also be employed. The equipment used for such heat treatment may use a static or flowing atmosphere of such gases to effect reduction, but a flowing atmosphere is much preferred.

In yet another embodiment of the present invention, after impregnation of the carrier with silver solution and before any roasting step, the impregnated carrier is rinsed with a silver compound solubilizing agent. This rinsing step helps remove excess silver that is present on the surface of the support thereby helping to avoid occlusion and/or agglomeration that may have been caused by such removed excess silver. This helps to maintain the porosity of the carrier and prevent its pores from becoming plugged with agglomerated silver particles. Conditions for such a rinsing step should be mild enough such that essentially only the excess surface silver is removed. Generally, a solvent is contacted with the impregnated support, without mixing, for up to about one minute, and then drained.

A consideration in making the catalyst of this invention is to avoid the use of strongly acidic or basic solutions which can attack the support and deposit impurities which can adversely affect the performance of the catalyst. The preferred impregnation procedure of U.K. Patent 2,043,481 coupled with the high roasting temperature, short residence time procedure which the patent also described is especially beneficial in minimizing such catalyst contamination. However, the use of promoter salts coupled with the high purity supports allows one to use lower temperatures though short residence times are preferred.

The particle size of silver metal deposited upon the carrier is asserted by a portion of the prior art to be a function of the catalyst preparation procedure employed. This may seem to be the case because of the limited ability of presently available analytical techniques to effectively view the surface of the catalyst. Thus the space between the silver particles seen on the carrier has not been characterized sufficiently to say whether only such particles of silver represent the silver on the carrier. However, the particular choice of solvent and/or complexing agent, silver compound, heat treatment conditions and catalyst carrier may affect, to varying degrees, the range of the size of the resulting silver particles seen on the carrier. For carriers of general interest for the production of ethylene oxide, a distribution of silver particle sizes in the range of 0.005 to 2.0 microns is typically obtained.

The silver catalysts of the invention are particularly suitable for use in the production of ethylene oxide by the vapor phase oxidation of ethylene with molecular oxygen. The reaction conditions for carrying out the oxidation reaction are well-known and extensively described in the prior art. This applies to reaction conditions, such as temperature, pressure, residence time, concentration of reactants, gas phase diluents (e.g., nitrogen, methane and $CO_2$), gas phase inhibitors (e.g., ethylene chloride and ethylene dichloride), and the like.

The gases fed to the reactor may contain modifiers or inhibitors or additives such as disclosed by Law, et al., in U.S. Pat. Nos. 2,279,469 and 2,279,470, such as nitrogen oxides and nitrogen oxide generating compounds.

European Patent No. 3642 employs catalysts comprising at least one efficiency-enhancing salt of a redox-half reaction pair in conjunction with at least one gaseous efficiency-enhancing member of a redox-half reaction pair.

The terms "gaseous member of a redox-half reaction pair", "gaseous efficiency-enhancing member of a redox-half reaction pair", or like terms referred to herein have a meaning similar to that for the "salt of a member of a redox-half reaction pair" or like terms, defined above. That is, these terms refer to members of half-reactions, represented in standard or single electrode potential tables in standard reference texts or handbooks which are in a gaseous state and are substances which, in the reaction equations represented in the texts, are either oxidized or reduced. The preferred gaseous efficiency-enhancing materials are compounds containing an element capable of existing in more than two valence states, preferably nitrogen and another element which is, preferably, oxygen. Examples of preferred gaseous efficiency-enhancing members of redox-half reaction pairs include at least one of NO, $NO_2$, $N_2O_4$, $N_2O_3$ or any gaseous substance capable of forming one of the aforementioned gases, particularly NO and $NO_2$, under epoxidation conditions, and mixtures thereof with one or more of $PH_3$, CO, $SO_3$, $SO_2$, $P_2O_5$, and $P_2O_3$. NO is often preferred as the gaseous efficiency-enhancing compound.

Although in some cases it is preferred to employ members of the same half-reaction pair in the reaction system, i.e., both the efficiency-enhancing salt member associated with the catalyst and the gaseous member in the feedstream, as, for example, with a preferred combination of potassium nitrate and nitric oxide, this is not necessary in all cases to achieve satisfactory results. Other combinations, such as $KNO_3/N_2O_3$, $KNO_3/NO_2$, $KNO_3/N_2O_4$, $KNO_3/SO_2$, $KNO_2/NO$, $KNO_2/NO_2$ and $KNO_3/a$ mixture of $SO_2$ and NO, may also be employed in the same system. In some instances, the salt and gaseous members may be found in different half-reactions which represent the first and last reactions in a series of half-reaction equations of an overall reaction.

The gaseous efficiency-enhancing member of a redox-half reaction pair is also present in an amount sufficient to enhance the performance, such as the activity of the catalyst, and, particularly, the efficiency of the epoxidation reaction. The precise amount is determined, in part, by the particular efficiency-enhancing salt of a member of a redox-half reaction pair used and the concentration thereof, the particular alkene undergoing oxidation, and by other factors noted above which influence the amount of efficiency-enhancing salt of a member of a redox-half reaction pair. Typically a suitable concentration of the gaseous member of a redox-half reaction pair for epoxidation of most alkenes, including propylene, is about 0.1 to about 2,000 ppm, by volume, of the gaseous feedstream when $N_2$ is used as ballast. When a preferred gaseous member of a redox-half reaction pair, such as NO, is used in the epoxidation of propylene, the preferred concentration is about 2,000 ppm, by volume, with an $N_2$ ballast. However, when ethylene is being oxidized, a suitable concentration for ethylene is from about 0.1 to about 100 ppm, by volume, of the gaseous feedstream components. Preferably, the gaseous efficiency-enhancing member of a redox-half reaction pair is present in an amount of about 1 to about 80 ppm when about 3 percent, by volume, $CO_2$ is present in the reaction mixture. When nitric oxide is employed as the gaseous efficiency-enhancing compound in an ethylene epoxidation system and $CO_2$ is present in the reaction mixture, e.g., in amounts up to about 3 volume percent, nitric oxide is present in an amount of about 0.1 to about 60 ppm, preferably about 1 to about 40 ppm.

The desirability of recycling unreacted feed, or employing a single-pass system, or using successive reactions to increase ethylene conversion by employing reactors in series arrangement can be readily determined by those skilled in the art. The particular mode of operation selected will usually be dictated by process economics.

Generally, the commercially-practiced processes are carried out by continuously introducing a feed stream containing ethylene and oxygen to a catalyst-containing reactor at a temperature of from about 200° C. to 300° C., and a pressure which may vary from about five atmospheres to about 30 atmospheres depending upon the mass velocity and productivity desired. Residence times in large-scale reactors are generally on the order of about 0.1–5 seconds. Oxygen may be supplied to the reaction in an oxygen-containing stream, such as air or as commercial oxygen. The resulting ethylene oxide is separated and recovered from the reaction products using conventional methods.

In commercial processes, typical operating conditions can vary and the amounts of the ingredients employed can be adjusted to achieve the best efficiencies. In particular the amounts of ethane, carbon dioxide and organic chloride can be varied to optimize efficiency for the manufacture of ethylene oxide. Ethane is an impurity contained in varying amounts in ethylene raw material. Ethane can also be added to a commercial reactor to provide better control of the chloride's inhibitor action. Typically, the amount of ethane used in commercial processes can vary from about 0.001 to about 5 mole percent for achieving optimization under both air process conditions and oxygen process conditions. As the concentration of ethane increases in the reactor, the effective surface chloride concentration on the catalyst is believed to be decreased thereby decreasing the ability of chloride to promote/inhibit reactions that increase efficiency for the manufacture of alkylene oxide. The amount of chloride, e.g., ethyl chloride or ethylene dichloride, can be varied to provide the needed promoter/inhibitor action commensurate with the ethane levels encountered in a particular process and the type of promoters or modifiers used in the catalyst. The amount of organic chloride used in commercial processes can typically vary from about 0.1 ppm to about 100 ppm for achieving optimization under both air process conditions and oxygen process conditions.

Carbon dioxide is generally considered an inhibitor, and the inhibiting effect of carbon dioxide on process efficiency may be variable with its concentration. With different types of promoters or modifiers used in preparation of the catalysts of this invention, different concentrations of carbon dioxide may be more desirable in certain commercial processes. Typically, the amount of carbon dioxide used in commercial processes can vary from about 2 to about 15 mole percent for achieving optimization under both air process conditions and oxygen process conditions. The amount of carbon dioxide is dependent on the size and type of carbon dioxide scrubbing system employed. The optimization of the amounts of ethane, carbon dioxide and organic chloride provides catalysts which are especially suitable for obtaining desired efficiencies in commercial ethylene oxide manufacture.

As a basis for convenient comparison with the prior art, the STANDARD ETHYLENE OXIDE PROCESS CONDITIONS have been defined herein and many of the following examples were conducted under those CONDITIONS. However, to also demonstrate that the catalysts of the present invention are capable of effectively operating at a variety of different epoxidation processing conditions and to also show the optimization of such conditions, many of the following examples were also conducted, as specifically noted therein, at conditions other than those of the STANDARD ETHYLENE OXIDE PROCESS CONDITIONS.

It is to be understood, of course, as is well recognized by those skilled in the art, that the efficiency of an epoxidation process for a given catalyst at a given set of processing conditions cannot indiscriminately be compared to the efficiency of an epoxidation process for that very same catalyst under different processing conditions.

EXAMPLES

The following detailed procedures are provided as illustrative of methods and carriers which are useful for preparing catalysts according to the invention. These examples are by way of illustration only and are not to be construed as limiting the scope of the invention described herein. In the examples, all parts and percentages of solids and liquids are by weight and gases by volume unless otherwise noted or clear from the context.

The carrier, as indicated, is impregnated under vacuum as hereinafter described with a solution of silver complex and alkali metal and/or alkaline earth metal salts. The alkali metal and/or alkaline earth metal-containing components need not be introduced as the salts. For instance, cesium hydroxide may be used in conjunction with an ammonium salt (e.g., ammonium sulfate) or acid (e.g., sulfuric acid) or organic compound (e.g., ethylsulfonate) and under conditions of catalyst preparation or use, conversion is made to the desired species. The impregnating solutions are prepared at concentrations such that the finished catalyst contained the desired amounts of silver and promoter or modifier. The required concentration of silver and promoter in solution for the given carrier is calculated from the packing density (grams/cc) and water pore volume of the carrier which are either known or readily determined. The relationship can vary depending upon the nature of the carrier, e.g., pore volume may influence the amount of silver deposited from a given solution. The required concentration of promoter in solution is obtained by dividing the solution silver concentration by the ratio of silver to promoter desired in the finished catalyst. As noted earlier, due to the high amount of silver required in the catalysts of the present invention, at least two or more impregnations are generally required.

In preparing the catalysts, generally a desired amount of ethylenediamine (high purity grade) is mixed with indicated amounts of distilled water. Then oxalic acid dihydrate (reagent grade) is then added slowly to the solution at ambient temperature (23° C.) while continuously stirring. During this addition of oxalic acid, the solution temperature typically rises to about 40° C. due to the reaction exotherm. Silver oxide powder is then added to the diamine-oxalic acid salt-water solution while maintaining the solution temperature below about 40° C. Finally, monoethanolamine, aqueous alkali metal salt solution(s) and distilled water are added to complete the solution.

Carrier can be impregnated in a vessel equipped with a suitable stopcock for draining the carrier after impregnation, however, other suitable flask sizes and types can be used. A suitable size separatory funnel for containing the impregnating solution is attached to the top of the impregnating vessel, which vessel is equipped with a vacuum line. The impregnating vessel containing the carrier is evacuated to approximately 1 to 2 inches of mercury pressure (absolute) for about 20 minutes after which the impregnating solution is slowly added to the carrier by opening the stopcock between the separatory funnel and the impregnating vessel until the carrier is completely immersed in solution, the pressure within the vessel being maintained at a pressure approximately 2 inches of mercury (absolute). Following addition of the solution, the vessel is opened to the atmosphere to attain atmospheric pressure. The carrier then remains immersed in the impregnating solution at ambient conditions for about 1 hour, and thereafter is drained of excess solution for about 15 to 30 minutes. The impregnated carrier is then heat treated as follows (unless stated otherwise) to effect reduction of silver salt and deposition of promoter on the surface. The impregnated carrier is spread out in a single layer on a $2\frac{5}{8}$ inches wide endless stainless steel belt (spiral weave) and transported through a 2 inches by 2 inches square heating zone for 2.5 minutes, the heating zone being maintained at 500° C. by passing hot air upward through the belt and about the catalyst particles at the rate of 266 SCFH. The hot air is generated by passing it through a 5 ft. long by 2 inches I.D. stainless steel pipe which was externally heated by an electric furnace (Lindberg TM tubular furnace: $2\frac{1}{2}$ inches I.D., 3 feet long heating zone) capable of delivering 5400 watts. The heated air in the pipe is discharged from a square 2 inches by 2 inches discharge port located immediately beneath the moving belt carrying the catalyst carrier. After being roasted in the heating zone, the finished catalyst is weighed, and based upon the weight gain of the carrier, and the known ratios of silver to promoter in the impregnating solution, it is calculated to contain the wt. % of silver, and ppm of promoter(s) indicated.

The following discussion is applicable to all examples.

The analysis for silver is carried out by the following method: An approximately 50 g sample of catalyst is powdered in a mill and 10 g of the powdered sample weighed to the nearest 0.1 mg. The silver in the catalyst sample is dissolved in hot (80° C.), 50% by volume, nitric acid solution. The insoluble alumina particles are filtered and washed with distilled water to remove all adhering nitrate salts of Ag, Cs, etc. This solution is made up to 250 ml in a volumetric flask using distilled water. A 25 ml aliquot of this solution is titrated according to standard procedures using a 0.1 Normal solution of ammonium thiocyanate and ferric nitrate as indicator. The amount of Ag so determined in 250 ml solution is then used to calculate the weight percent silver in the catalyst sample.

Silver and promoter concentrations for all catalysts described in the specification are calculated values as described above, except where otherwise indicated.

Carriers are nominally ring shape having dimensions of about $\frac{1}{8} \times 5/16 \times 5/16$ inch or about $\frac{1}{4} \times \frac{1}{4} \times \frac{1}{4}$ inch.

In Table 1 below, a detailed chart is set forth defining the content and mode of preparing each of the catalysts tested in examples 1 to 78. The amount of support and the reagents used for each impregnation step for each catalyst are also set forth. Also included in this table is a reference to the particular support number used in preparing the catalyst. The properties of those supports are detailed in a chart set forth in Table 2 below.

In preparing the data for Table 2, the surface area of the supports are determined by the method of measurement described in "Adsorption Surface Area and Porosity", S. J. Gregg and K. S. W. Sing, *Academic Press* (1967), pages 316–321. The method of measurement for the pore volume is described in ASTM C20-46. The calculated value of the packing density is based on conventional measurement of the weight of the carrier in a known volume container. The method of measurement for the median pore diameter is described in "Application of Mercury Penetration to Materials Analysis", C. Orr, Jr., *Powder Technology*, Vol. 3, pp. 117–123 (1970).

Crush Strength Average and Range is determined according to Test No. 6 as referred to in Catalyst Carriers Norton Company, Akron, Ohio Bulletin CC-11, 1974. Acid Leachable Impurities are determined by contacting carrier pills with 10% nitric acid for one hour at about 90° C. and determining extracted cations by standard Atomic Absorption spectroscopy techniques. Inductively Coupled Plasma Spectroscopy techniques may also be used for such determinations.

The identity and amounts of water leachable components of carriers can be determined by any convenient analytical technique. Generally, the carriers are heated in distilled water, e.g., as condensate from a recycling reflux apparatus, at a temperature of about 50° to 95° C., often 90° C., for about 0.5 to 2, e.g., 1 hour. The liquid is then subjected to ion chromatography and Inductively Coupled Plasma Spectroscopy techniques.

Surface acidity is determined by the ammonia chemisorption method. A conventional glass vacuum/adsorption apparatus with a base pressure of $1 \times 10^{-6}$ Torr is used for this purpose. Grease-free stopcocks are used to avoid contamination. Approximately 10 to 15 grams of sample (whole pills or 14/30 mesh) are pretreated in flowing (40 cc/min) helium at 200° C. for 1 hour followed by 15 minutes evacuation at this temperature. Samples are cooled in vacuum to 100° C. for acidity measurements.

The ammonia chemisorption is measured in a static mode by volumetric method at 100° C. Samples are exposed to a known amount of ammonia (15 Torr in a calibrated volume) for period of 45 minutes (or longer until no further ammonia uptake is detected). The ammonia consumption is measured by monitoring its pressure in the system. The ideal gas law is used to calculate the micromoles of ammonia sorbed. The sample is then evacuated for 15 minutes at 100° C., and the chemisorption measurement is repeated. The ammonia consumed in this second measurement is subtracted from the first ammonia sorption to provide the amount of ammonia irreversibly (or strongly) sorbed. This measurement is reported in micromoles of ammonia strongly absorbed per gram of sample as a report of sample acidity.

The catalysts that are set forth in Table 1 are prepared using the general procedures set forth below.

IMPREGNATION SOLUTION PREPARATION

The impregnation solution is prepared based on the pore volume of the unimpregnated support (given in Table 2) or that of a previously-impregnated and roasted support.

1. Ethylenediamine (high purity grade) is mixed with the distilled water.
2. Oxalic acid dihydrate (reagent grade) is slowly added to the aqueous ethylenediamine solution at ambient conditions. An exothermic reaction occurs and the solution temperature rises to about 40° C.
3. Silver oxide is then added slowly to the solution of step 2.
4. Monoethanolamine (Fe and Cl free) is then added to the solution of step 3.
5. Promoter salts dissolved in aqueous solution may or may not be added to solution 4 at this point (see Table 1). In some instances, promoters are added as solids to solution 4.
6. Distilled water is then added to adjust the solution volume.

Each catalyst is prepared by using one or more impregnations of a solution, made as described above with or without added promoter salts as detailed in Table 1. For either the first or subsequent impregnation(s), the solution may or may not contain promoter salts(s) (see Table 1). In addition, some catalysts were made by adding the promoter salts from aqueous solution only, i.e., not in the silver impregnating solution, after the final addition and roasting of silver-containing support (sequential promoter deposition).

IMPREGNATION OF THE CARRIER

1. The carrier is evacuated at room temperature and the appropriate impregnation solution (see Table 1) is added to the carrier under vacuum. The solution is allowed to contact the previously unimpregnated support (or previously impregnated and roasted support) for about 2 to about 60 minutes before draining.
2. The excess solution is drained off.

RINSING OF FRESHLY-IMPREGNATED SUPPORT

The freshly-impregnated support can be rinsed at this point to reduce the amount of large (occluding) silver particles on the external surfaces of the catalyst which sometimes can occur upon roasting. The rinsing solution used after an impregnation using a solution which does not contain promoters is essentially the same impregnation solution except it now is devoid of the silver oxide and monoethanolamine, i.e., it is a solution of ethylenediamine, water and oxalic acid. The rinsing solution that is used after a final impregnation which contains promoters is essentially the same impregnation solution still containing promoter(s) and ethanolamine but now devoid of silver oxide. The rinsing solution is then allowed to drain from the material through the exit stopcock of the impregnating tube for approximately 5 minutes.

CATALYST ROASTING

The impregnated carrier (with or without rinsing) is roasted in hot air using a belt roaster at about 500° C. for about 2.5 minutes. Air flow is 66 SCFH/in$^2$.

The catalysts were tested at the specific conditions noted in each of the following Tables 3 through 17.

TABLE 1

CATALYST PREPARATIONS

| | CATALYST NUMBER | | | | | | | | | |
|---|---|---|---|---|---|---|---|---|---|---|
| | 1 | 2 | 3 | 4 | 5 | 6 | 6 CONT | 7 | 8 | 9 |
| First Impregnation | | | | | | | 4th Imp. | | | |
| Support Number | A | B | A | A | A | A | A | C | C | C |
| grams Support | 35.73 | 2743.00 | 44.47 | 108.60 | 44.02 | 43.17 | 71.56 | 93.71 | 293.13 | 1876.00 |
| grams Ethlenediamine | 8.41 | 1220.20 | 23.00 | 17.48 | 17.48 | 20.13 | 20.13 | 53.26 | 196.75 | 1259.20 |
| grams Oxalic Acid | 8.42 | 1245.10 | 23.00 | 17.50 | 17.50 | 20.16 | 20.16 | 53.78 | 197.06 | 1261.20 |
| grams Silver Oxide | 14.75 | 1962.00 | 43.34 | 30.66 | 30.66 | 35.31 | 35.31 | 93.42 | 345.19 | 2209.30 |
| grams Monoethanolamine | 2.95 | 460.00 | 8.07 | 6.13 | 6.13 | 7.06 | 7.06 | 18.68 | 195.00 | 442.10 |
| grams Distilled Water | 8.33 | 1200.50 | 30.00 | 17.32 | 17.32 | 19.95 | 19.95 | 52.78 | 69.06 | 1248.00 |
| grams Promoter | | 101.4, | 0.4234 | | | | | | | |

TABLE 1-continued

CATALYST PREPARATIONS

| | | | | | | | | | | |
|---|---|---|---|---|---|---|---|---|---|---|
| grams Promoter | | KNO3 | KNO3 | | | | | | | |
| grams Promoter | | | | | | | | | | |
| ppm Promoter Pick-up | | 3789 | 814 | | | | | | | |
| ppm Promoter Pick-up | | | | | | | | | | |
| ppm Promoter Pick-up | | | | | | | | | | |
| % Silver Pick-up | 8.3 | 17.8 | 20.1 | 11.7 | 15.5 | 17.6 | 11.1 | 22.2 | 24.6 | 24.5 |
| Second Impregnation | | | | | | | | | | |
| grams Ethylenediamine | | | | | 17.48 | 20.13 | | | 37.54 | 1196.20 |
| grams Oxalic Acid | | | | | 17.50 | 20.16 | | | 37.60 | 1198.10 |
| grams Silver Oxide | | | | | 30.66 | 35.31 | | | 65.86 | 2098.70 |
| grams Monoethanolamine | | | | | 6.13 | 7.06 | | | 13.17 | 419.90 |
| grams Distilled Water | 100.00 | | | 100.00 | 117.32 | 19.95 | 100.00 | 100.00 | 37.20 | 5185.60 |
| grams Promoter | 0.79, KNO3 | | | 2.12, KNO3 | 1.18, KNO3 | | 1.05, KNO3 | 0.29, KNO3 | 0.4, KNO3 | 24.8, KNO3 |
| grams Promoter | | | | | | | | | | |
| grams Promoter | | | | | | | | | | |
| % Silver Pick-up | | | | | | 15.6 | | | | |
| Total Silver Pick-up | | | | 34.8 | 36.6 | | 46.4 | 36.0 | 39.2 | 38.5 |
| ppm Promoter Pick-up | 2300,K | | | 3310,K | 1730,K | | 1420,K | 450,K | 487,K | 1024,K |
| ppm Promoter Pick-up | | | | | | | | | | |
| ppm Promoter Pick-up | | | | | | | | | | |
| Third Impregnation | | | | | | | | | | |
| grams Ethylenediamine | | | | | | 20.13 | | | | |
| grams Oxalic Acid | | | | | | 20.16 | | | | |
| grams Silver Oxide | | | | | | 35.31 | | | | |
| grams Monoethanolamine | | | | | | 7.06 | | | | |
| grams Distilled Water | | | | | | 19.95 | | | | |
| grams Promoter | | | | | | | | | | |
| grams Promoter | | | | | | | | | | |
| % Silver Pick-up | | | | | | 13.3 | | | | |
| Total Silver Pick-up | | | | | | | | | | |
| Total ppm Promoter | | | | | | | | | | |

| | CATALYST NUMBER | | | | | | | | | |
|---|---|---|---|---|---|---|---|---|---|---|
| | 10 | 11 | 12 | 13 | 14 | 15 | 16 | 17 | 18 | 19 |
| First Impregnation | | | | | | | | | | |
| Support Number | C | C | D | D | D | E | F | B | G | G |
| grams Support | 293.13 | 293.13 | 52.12 | 52.07 | 52.33 | 52.31 | 63.50 | 82.30 | 49.23 | 49.30 |
| grams Ethlenediamine | 196.75 | 196.75 | 36.75 | 36.94 | 36.72 | 21.60 | 1347.00 | 101.68 | 20.33 | 32.33 |
| grams Oxalic Acid | 197.06 | 197.06 | 36.80 | 36.82 | 36.80 | 21.64 | 1349.00 | 103.76 | 20.75 | 32.38 |
| grams Silver Oxide | 345.19 | 345.19 | 64.45 | 64.46 | 64.45 | 37.90 | 2363.00 | 181.64 | 36.33 | 56.72 |
| grams Monoethanolamine | 69.06 | 69.06 | 12.89 | 12.91 | 12.88 | 7.58 | 473.00 | 38.33 | 7.66 | 11.34 |
| grams Distilled Water | 195.00 | 195.00 | 36.41 | 37.03 | 36.42 | 21.41 | 1335.00 | 100.00 | 20.00 | |
| grams Promoter | | | | | | | | | 0.2121 RbNO3 | |
| grams Promoter | | | | | | | | | | |
| grams Promoter | | | | | | | | | | |
| ppm Promoter Pick-up | | | | | | | | | 2000,Rb | |
| ppm Promoter Pick-up | | | | | | | | | | |
| ppm Promoter Pick-up | | | | | | | | | | |
| % Silver Pick-up | 24.6 | 24.6 | 24.8 | 20.6 | 22.0 | | | 20.3 | 19.7 | 25.8 |
| Second Impregnation | | | | | | | | | | |
| grams Ethylenediamine | 37.54 | 37.54 | 36.75 | 36.94 | 36.72 | | 32.85 | | | 32.33 |
| grams Oxalic Acid | 37.60 | 37.60 | 36.80 | 36.82 | 36.80 | | 32.90 | | | 32.38 |
| grams Silver Oxide | 65.86 | 65.86 | 64.45 | 64.46 | 64.45 | | 57.63 | | | 56.72 |
| grams Monoethanolamine | 13.17 | 13.17 | 12.89 | 12.91 | 12.88 | | 11.53 | | | 11.34 |
| grams Distilled Water | 37.20 | 37.20 | 36.41 | 37.03 | 36.42 | 15.00 | 47.55 | 31.00 | | 32.04 |
| grams Promoter | 0.4, KNO3 | 1.19, KNO3 | 0.8117 KNO3 | 0.8117 KNO3 | 0.4058 KNO3 | 0.4895, KNO3 | 0.8396, KNO3 | 0.1319 KNO3 | | 0.2846 RbNO3 |
| grams Promoter | | | | | | | | | | |
| grams Promoter | | | | | | | | | | |
| % Silver Pick-up | | | 14.4 | 16.1 | 14.4 | | | | | 14.6 |
| Total Silver Pick-up | 39.2 | 39.3 | 39.2 | 36.7 | 36.4 | 17.7 | 32.1 | 20.3 | | 39.9 |
| ppm Promoter Pick-up | 487,K | 1500,K | 978,K | 918,K | 910,K | 972,K | 1036,K | 500,K | | 3000,Rb |
| ppm Promoter Pick-up | | | | | | | | | | |
| ppm Promoter Pick-up | | | | | | | | | | |
| Third Impregnation | | | | | | | | | | |
| grams Ethylenediamine | | | | | | | 32.85 | | | |
| grams Oxalic Acid | | | | | | | 32.90 | | | |
| grams Silver Oxide | | | | | | | 57.63 | | | |
| grams Monoethanolamine | | | | | | | 11.53 | | | |
| grams Distilled Water | | | | | | | 47.55 | | | |
| grams Promoter | | | | | | | 0.8437, KNO3 | | | |
| grams Promoter | | | | | | | | | | |
| % Silver Pick-up | | | | | | | | | | |
| Total Silver Pick-up | | | | | | | 32.2 | | | |
| Total ppm Promoter | | | | | | | 1011,K | | | |

TABLE 1-continued

CATALYST PREPARATIONS

| | CATALYST NUMBER | | | | | | | | | |
|---|---|---|---|---|---|---|---|---|---|---|
| | 20 | 21 | 22 | 23 | 24 | 25 | 26 | 27 | 28 | 29 |
| First Impregnation | | | | | | | | | | |
| Support Number | G | H | H | B | D | I | D | J | J | K |
| grams Support | 1500.00 | 1500.00 | 1500.00 | 1317.00 | 1500.00 | 2064.50 | 1500.00 | 53.82 | 59.39 | 60.39 |
| grams Ethlenediamine | 1175.67 | 881.75 | 881.75 | 772.67 | 881.75 | 1352.00 | 881.75 | 27.33 | 237.26 | 28.58 |
| grams Oxalic Acid | 1177.50 | 883.13 | 883.13 | 772.67 | 883.13 | 1353.60 | 883.13 | 27.38 | 238.00 | 28.67 |
| grams Silver Oxide | 2062.50 | 1546.88 | 1546.88 | 1456.10 | 1546.88 | 2371.20 | 1546.88 | 47.38 | 413.20 | 48.77 |
| grams Monoethanolamine | 412.50 | 309.38 | 309.38 | 271.11 | 309.38 | 474.40 | 309.38 | 9.59 | 87.73 | 10.57 |
| grams Distilled Water | 1165.17 | 873.88 | 873.88 | 1000.00 | 873.88 | 1339.60 | 873.88 | 25.00 | 200.20 | 26.00 |
| grams Promoter | | | | 9.7845, KNO3 | | | | 0.166, Cs2SO4 | | 0.5067, Cs2SO4 |
| grams Promoter | | | | | | | | | | |
| grams Promoter | | | | | | | | | | |
| ppm Promoter Pick-up | | | | 563 | | | | 544 | | 723 |
| ppm Promoter Pick-up | | | | | | | | | | |
| ppm Promoter Pick-up | | | | | | | | | | |
| % Silver Pick-up | 25.3 | 25.7 | 25.2 | 20.2 | 25.5 | 23.2 | 26.1 | 19.9 | 19.0 | 19.9 |
| Second Impregnation | | | | | | | | | | |
| grams Ethylenediamine | 1175.67 | 881.75 | 881.75 | | 881.75 | 1352.00 | 881.75 | | 237.26 | |
| grams Oxalic Acid | 1177.50 | 883.13 | 883.13 | | 883.13 | 1353.60 | 883.13 | | 238.00 | |
| grams Silver Oxide | 2062.50 | 1546.88 | 154.88 | | 1546.88 | 2371.20 | 1546.88 | | 413.20 | |
| grams Monoethanolamine | 412.50 | 309.38 | 309.38 | | 309.38 | 474.40 | 309.38 | | 87.73 | |
| grams Distilled Water | 1165.17 | 1546.88 | 873.88 | | 873.88 | 1339.60 | 873.88 | | 200.20 | |
| grams Promoter | 47.09, RbNO3 | 12.36, RbNO3 | 26.89, RbNO3 | | 19.48, KNO3 | 9.471, KNO3 | 11.69, KNO3 | | 0.130, Cs2SO4 | |
| grams Promoter | | | | | | | | | | |
| grams Promoter | | | | | | | | | | |
| % Silver Pick-up | 14.6 | 13.3 | 14.0 | | 14.7 | | 14.8 | | | |
| Total Silver Pick-up | 39.9 | 39.2 | 39.1 | | 40.1 | 37.9 | 40.9 | | 31.8 | |
| ppm Promoter Pick-up | 3000,Rb | 921,Rb | 2000,Rb | | 1000,K | 318,K | 600,K | | 554,Cs | |
| ppm Promoter Pick-up | | | | | | | | | | |
| ppm Promoter Pick-up | | | | | | | | | | |
| Third Impregnation | | | | | | | | | | |
| grams Ethylenediamine | | | | | | | | | | |
| grams Oxalic Acid | | | | | | | | | | |
| grams Silver Oxide | | | | | | | | | | |
| grams Monoethanolamine | | | | | | | | | | |
| grams Distilled Water | | | | | | | | | | |
| grams Promoter | | | | | | | | | | |
| grams Promoter | | | | | | | | | | |
| % Silver Pick-up | | | | | | | | | | |
| Total Silver Pick-up | | | | | | | | | | |
| Total ppm Promoter | | | | | | | | | | |

| | CATALYST NUMBER | | | | | | | | | |
|---|---|---|---|---|---|---|---|---|---|---|
| | 30 | 31 | 32 | 33 | 34 | 35 | 36 | 37 | 38 | 39 |
| First Impregnation | | | | | | | | | | |
| Support Number | K | L | L | J | L | Q | R | R | R | G |
| grams Support | 60.59 | 53.06 | 53.08 | 53.08 | 53.17 | 60.05 | 60.13 | 60.12 | 61.54 | 1900.00 |
| grams Ethlenediamine | 27.48 | 28.23 | 28.23 | 28.23 | 28.22 | 21.10 | 27.80 | 27.80 | 27.80 | 845.08 |
| grams Oxalic Acid | 27.57 | 28.27 | 53.77 | 28.27 | 28.27 | 21.10 | 27.80 | 27.80 | 27.80 | 845.60 |
| grams Silver Oxide | 47.86 | 49.52 | 49.51 | 49.52 | 49.51 | 37.02 | 48.77 | 48.77 | 48.77 | 1480.96 |
| grams Monoethanolamine | 10.16 | 9.90 | 9.93 | 9.90 | 9.90 | 7.89 | 9.77 | 9.77 | 9.77 | 296.15 |
| grams Distilled Water | 25.00 | 25.00 | 25.50 | 25.00 | 25.00 | 75.00 | 60.00 | 64.50 | 64.50 | 851.50 |
| grams Promoter | | 0.2146, Cs2SO4 | | 0.2131, Cs2SO4 | | 0.2024, Cs2SO4 | 0.1629, Cs2SO4 | 0.122, Cs2SO4 | 0.1067, Cs2SO4 | |
| grams Promoter | | | | 0.1029, K2SO4 | | | | | | |
| grams Promoter | | | | | | | | | | |
| ppm Promoter Pick-up | | 687 | | 709,Cs | | 699,Cs | 528,Cs | | | |
| ppm Promoter Pick-up | | | | 209,Cs | | | | | | |
| ppm Promoter Pick-up | | | | | | | | | | |
| % Silver Pick-up | 20.9 | 20.4 | | 21.0 | 20.4 | 16.2 | 20.1 | | | |
| Second Impregnation | | | | | | | | | | |
| grams Ethylenediamine | 27.48 | | 28.23 | | 28.22 | | | 27.51 | 27.80 | 844.85 |
| grams Oxalic Acid | 27.57 | | 53.77 | | 28.27 | | | 27.21 | 27.80 | 845.60 |
| grams Silver Oxide | 47.86 | | 49.51 | | 49.51 | | | 48.26 | 48.77 | 1480.96 |
| grams Monoethanolamine | 10.16 | | 9.93 | | 9.90 | | | 9.67 | 9.77 | 296.17 |
| grams Distilled Water | 25.00 | | 25.50 | | 25.00 | | | 27.21 | 63.50 | 850.10 |
| grams Promoter | 3.92, KNO3 | | 0.2669, Cs2SO4 | | 0.2667, Cs2SO4 | | | 0.122, Cs2SO4 | 0.131, Cs2SO4 | 11.73, Cs2SO4 |
| grams Promoter | | | | | 0.1283, K2SO4 | | | | | |
| grams Promoter | | | | | | | | | | |
| % Silver Pick-up | | | | | | | | 12.4 | 13.1 | 31.7 |
| Total Silver Pick-up | 33.0 | | 33.9 | | 32.3 | | | 33.5 | 33.0 | 31.9 |
| ppm Promoter Pick-up | 842,K | | 709 | | 693,Cs | | | 641,Cs | 585,Cs | 1016,Cs |
| ppm Promoter Pick-up | | | | | 203,K | | | | | |

TABLE 1-continued
CATALYST PREPARATIONS ppm Promoter Pick-up
Third Impregnation
grams Ethylenediamine
grams Oxalic Acid
grams Silver Oxide
grams Monoethanolamine
grams Distilled Water
grams Promoter
grams Promoter
% Silver Pick-up
Total Silver Pick-up
Total ppm Promoter

| | CATALYST NUMBER | | | | | | | | | |
|---|---|---|---|---|---|---|---|---|---|---|
| | 40 | 41 | 42 | 43 | 44 | 45 | 46 | 47 | 48 | 49 |
| First Impregnation | | | | | | | | | | |
| Support Number | D | I | S | S | I | L | L | L | L | L |
| grams Support | 2000.00 | 10.00 | 5.50 | 535.00 | 30.40 | 24.40 | 50.52 | 55.56 | 49.20 | 29.00 |
| grams Ethlenediamine | 917.00 | 36.00 | 2.31 | 203.0 | 12.70 | 5.80 | 28.22 | 32.05 | 12.50 | 17.60 |
| grams Oxalic Acid | 917.50 | 3.60 | 2.31 | 203.0 | 12.70 | 5.80 | 28.27 | 32.11 | 12.50 | 17.60 |
| grams Silver Oxide | 1596.50 | 6.40 | 4.05 | 356.00 | 22.30 | 9.50 | 49.51 | 56.23 | 22.00 | 30.90 |
| grams Monoethanolamine | 338.90 | 1.40 | 0.81 | 71.00 | 4.50 | 2.10 | 9.90 | 11.25 | 4.40 | 6.18 |
| grams Distilled Water | 800.00 | 10.30 | 8.59 | 774.00 | 64.00 | 47.40 | 62.60 | 5.38 | 48.20 | 19.00 |
| grams Promoter | 6.556, $Cs_2SO_4$ | | | 1.53, $Cs_2MoO_4$ | 0.096 $Cs_2MoO_4$ | 0 | 0.1197 $CsMoO_4$ | 0 | 0 | 0 |
| grams Promoter | 3.7661, $K_2SO_4$ | | | | | | 0.0550 $Cs_2SO_4$ | | | |
| grams Promoter | | | | | | | 0.0719 $Rb_2SO_4$ | | | |
| ppm Promoter Pick-up | 597,Cs | | | 500,Cs | | | 325, Cs(Mo) | | | |
| ppm Promoter Pick-up | 185,K | | | | | | 175, Cs(SO4) | | | |
| ppm Promoter Pick-up | | | | | | | 200,Rb | | | |
| % Silver Pick-up | 20.6 | 18.3 | 16.2 | 15.1 | 15.3 | 10.0 | 21.4 | 22.7 | 10.4 | 26.7 |
| Second Impregnation | | | | | | | | | | |
| grams Ethylenediamine | | 15.00 | 6.35 | | 12.70 | 8.80 | | 15.94 | 35.10 | 17.60 |
| grams Oxalic Acid | | 0.00 | 6.35 | | 12.70 | 8.80 | | 15.90 | 35.10 | 17.70 |
| grams Silver Oxide | | 0.00 | 0.00 | | 22.30 | 15.40 | | 28.00 | 61.50 | 30.90 |
| grams Monoethanolamine | | 0.00 | 2.23 | | 4.50 | 3.0 | | 5.60 | 12.30 | 6.20 |
| grams Distilled Water | | 32.20 | 25.11 | | 64.00 | 44.30 | | 89.60 | 47.30 | 21.00 |
| grams Promoter | | 0.066, $Cs_2MoO_4$ | 0.05, $Cs_2MoO_4$ | | 0.096, $Cs_2MoO_4$ | 0.0597 $Cs_2MoO_4$ | | 0.157 $Cs_2MoO_4$ | 0.1524 $Cs_2MoO_4$ | 0.0658 $Cs_2MoO_4$ |
| grams Promoter | | | | | | 0.0284 $Cs_2SO_4$ | | 0.0691 $Cs_2SO_4$ | 0.0701 $Cs_2SO_4$ | 0.0302 $Cs_2SO_4$ |
| grams Promoter | | | | | | 0.0363 $Rb_2SO_4$ | | 0.0942 $Rb_2SO_4$ | 0.0918 $Rb_2SO_4$ | 0.0398 $Rb_2SO_4$ |
| % Silver Pick-up | | 0.0 | 0.0 | | 13.6 | 12.0 | | 10.4 | 22.6 | 19.6 |
| Total Silver Pick-up | | 18.3 | 16.2 | | 26.9 | 20.0 | | 30.7 | 30.6 | 41.0 |
| ppm Promoter Pick-up | | 520,Cs | 517,Cs | | 500,Cs | 325, Cs(Mo) | | 360, Cs(Mo) | 360, Cs(Mo) | 360, Cs(Mo) |
| ppm Promoter Pick-up | | | | | | 175, Cs(SO4) | | 190, Cs(SO4) | 190, Cs(SO4) | 190, Cs(SO4) |
| ppm Promoter Pick-up | | | | | | 200,Rb | | 220,Rb | 220,Rb | 220,Rb |

Third Impregnation
grams Ethylenediamine
grams Oxalic Acid
grams Silver Oxide
grams Monoethanolamine
grams Distilled Water
grams Promoter
grams Promoter
% Silver Pick-up
Total Silver Pick-up
Total ppm Promoter

| | CATALYST NUMBER | | | | | | | | | |
|---|---|---|---|---|---|---|---|---|---|---|
| | 50 | 51 | 52 | 53 | 54 | 55 | 56 | 57 | 58 | 59 |
| First Impregnation | | | | | | | | | | |
| Support Number | T | T | T | D | D | D | M | M | N | N |
| grams Support | 26.30 | 26.60 | 22.70 | 24.20 | 26.40 | 24.40 | 69.37 | 65.42 | 65.50 | 62.21 |
| grams Ethlenediamine | 7.80 | 15.50 | 12.30 | 5.50 | 5.30 | 5.50 | 32.51 | 33.81 | 27.15 | 27.09 |
| grams Oxalic Acid | 7.80 | 15.60 | 12.30 | 5.50 | 5.40 | 5.50 | 32.61 | 33.91 | 27.23 | 27.17 |
| grams Silver Oxide | 13.70 | 27.20 | 21.60 | 9.60 | 9.40 | 9.70 | 56.61 | 58.87 | 47.28 | 47.18 |
| grams Monoethanolamine | 2.70 | 5.40 | 4.30 | 1.90 | 1.90 | 1.90 | 12.02 | 12.50 | 10.04 | 10.02 |
| grams Distilled Water | 51.50 | 29.00 | 24.00 | 46.00 | 47.00 | 48.00 | 25.00 | 26.00 | 25.00 | 26.00 |
| grams Promoter | 0 | 0 | 0 | 0 | 0 | 0 | | 2.62, $Cs_2SO_4$ | | 6,$Cs_2SO_4$ |
| grams Promoter | | | | | | | | | | |

TABLE 1-continued
CATALYST PREPARATIONS

| | | | | | | | | | |
|---|---|---|---|---|---|---|---|---|---|
| grams Promoter | | | | | | | | | |
| ppm Promoter Pick-up | | | | | | | | 403 | 749 |
| ppm Promoter Pick-up | | | | | | | | | |
| ppm Promoter Pick-up | | | | | | | | | |
| % Silver Pick-up | 12.1 | 21.3 | 21.0 | 10.3 | 10.0 | 10.3 | | 20.1 | 19.5 |
| Second Impregnation | | | | | | | | | |
| grams Ethylenediamine | 21.00 | 23.20 | 23.30 | 17.60 | 17.70 | 17.60 | 32.51 | | 27.15 |
| grams Oxalic Acid | 21.10 | 23.30 | 23.30 | 17.70 | 17.70 | 17.70 | 32.61 | | 27.23 |
| grams Silver Oxide | 36.90 | 40.80 | 40.80 | 31.00 | 31.00 | 31.00 | 56.61 | | 47.28 |
| grams Monoethanolamine | 7.40 | 4.00 | 4.00 | 6.20 | 6.20 | 6.20 | 12.02 | | 10.04 |
| grams Distilled Water | 27.20 | 10.40 | 9.50 | 23.00 | 19.70 | 19.70 | 25.00 | | 25.00 |
| grams Promoter | 0.1077 Cs2MoO4 | 0.2554 Cs2SO4 | 0.5054 Cs2SO4 | 0.1325 Cs2SO4 | 0.0105 Cs2MoO4 | 0.1324 Cs2SO4 | 2.52 Cs2SO4 | | 4.03 Cs2SO4 |
| grams Promoter | 0.2750 Cs2SO4 | | 0.1008 Cs2MoO4 | | 0.124 Cs2SO4 | 0.0207 Cs2MoO4 | | | |
| grams Promoter | | | | | | | | | |
| % Silver Pick-up | 21.5 | 23.5 | 22.9 | 22.9 | 24.4 | 23.9 | | | |
| Total Silver Pick-up | 30.9 | 39.8 | 39.1 | 30.8 | 32.0 | 32.7 | 31.2 | | 33.6 |
| ppm Promoter Pick-up | 400, Cs(Mo) | 1200,Cs | 1200. Cs(SO4) | 750,Cs | 50, Cs(Mo) | 750, Cs(SO4) | 331,Cs | | 640,Cs |
| ppm Promoter Pick-up | 1200,Cs Cs(So4) | | 400, Cs(Mo) | | 700, Cs(SO4) | 100, Cs(Mo) | | | |
| ppm Promoter Pick-up | | | | | | | | | |
| Third Impregnation | | | | | | | | | |
| grams Ethylenediamine | | | | | | | | | |
| grams Oxalic Acid | | | | | | | | | |
| grams Silver Oxide | | | | | | | | | |
| grams Monoethanolamine | | | | | | | | | |
| grams Distilled Water | | | | | | | | | |
| grams Promoter | | | | | | | | | |
| grams Promoter | | | | | | | | | |
| % Silver Pick-up | | | | | | | | | |
| Total Silver Pick-up | | | | | | | | | |
| Total ppm Promoter | | | | | | | | | |

| | CATALYST NUMBER | | | | | |
|---|---|---|---|---|---|---|
| | 60 | 61 | 62 | 63 | 64 | 65 |
| First Impregnation | | | | | | |
| Support Number | O | O | K | K | P | P |
| grams Support | 63.68 | 60.32 | 60.06 | 60.39 | 27.82 | 28.65 |
| grams Ethlenediamine | 28.35 | 27.48 | 55.24 | 28.58 | 13.98 | 37.28 |
| grams Oxalic Acid | 28.44 | 27.57 | 55.41 | 28.67 | 14.03 | 37.39 |
| grams Silver Oxide | 49.37 | 47.86 | 96.19 | 49.77 | 24.35 | 64.92 |
| grams Monoethanolamine | 10.48 | 10.16 | 20.42 | 10.57 | 5.17 | 13.78 |
| grams Distilled Water | 25.00 | 25.00 | 50.00 | 26.00 | 26.00 | 26.00 |
| grams Promoter | 3.58 Cs2SO4 | | 3.92 Cs2SO4 | 4 Cs2SO4 | 3.02 Cs2SO4 | 3.289 Cs2SO4 |
| grams Promoter | | | | | | |
| grams Promoter | | | | | | |
| ppm Promoter Pick-up | 668 | | 794 | 723 | 875 | 938 |
| ppm Promoter Pick-up | | | | | | |
| ppm Promoter Pick-up | | | | | | |
| % Silver Pick-up | 20.4 | | 21.5 | 19.9 | 15.5 | 40.6 |
| Second Impregnation | | | | | | |
| grams Ethylenediamine | | 27.48 | | | | |
| grams Oxalic Acid | | 27.57 | | | | |
| grams Silver Oxide | | 47.86 | | | | |
| grams Monoethanolamine | | 10.16 | | | | |
| grams Distilled Water | | 25.00 | | | | |
| grams Promoter | | 5.4 Cs2SO4 | | | | |
| grams Promoter | | | | | | |
| grams Promoter | | | | | | |
| % Silver Pick-up | | | | | | |
| Total Silver Pick-up | | 33.3 | | | | |
| ppm Promoter Pick-up | | 848.Cs | | | | |
| ppm Promoter Pick-up | | | | | | |
| ppm Promoter Pick-up | | | | | | |
| Third Impregnation | | | | | | |
| grams Ethylenediamine | | | | | | |
| grams Oxalic Acid | | | | | | |
| grams Silver Oxide | | | | | | |
| grams Monoethanolamine | | | | | | |
| grams Distilled Water | | | | | | |
| grams Promoter | | | | | | |
| grams Promoter | | | | | | |
| % Silver Pick-up | | | | | | |
| Total Silver Pick-up | | | | | | |

TABLE 1-continued
CATALYST PREPARATIONS
Total ppm Promoter

NOTE:
Cs(Mo) = ppm Cs as the Molybdate
Cs(SO4) = ppm Cs as the Sulfate

TABLE 2
SUPPORT DATA

| PROPERTY | | A | B | C | D | E | F | G | H | I | J | K | L |
|---|---|---|---|---|---|---|---|---|---|---|---|---|---|
| Size (O.D.) | inches | 0.25 | 0.25 | 0.25 | 0.23 | 0.25 | 0.25 | 0.24 | 0.24 | 0.25 | 0.31 | 0.31 | 0.23 |
| Surface Area | m2g-1 | 1.60 | 1.25 | 1.20 | 1.08 | 1.30 | 0.52 | 2.01 | 1.66 | 1.10 | .93 | 1.51 | 1.16 |
| Water Pore Volume | % | 78.4 | 78.4 | 81.0 | 67.1 | 80.9 | 61.4 | 72.5 | 64.3 | 75.6 | 70.0 | 78.2 | 67.8 |
| Median Pore Diameter | microns | | | | 1.9 | | | 1.2 | 1.1 | | 2.3 | 1.6 | 1.8 |
| Residual Fluoride | % | 0.70 | 0.22 | 0.40 | 0.24 | 0.93 | 0.16 | 0.47 | 0.31 | 0.20 | 0.28 | 0.31 | 0.29 |
| Crush Strength | lbs | | | | 6.0 | | | 10.8 | 7.4 | | 6.9 | 16.5 | 6.4 |
| Water Leachables, ppm | | | | | | | | | | | | | |
| Phosphate | | | | | 30 | | | 3 | | | 7 | 1 | 11 |
| Fluoride | | | | | 375 | | | 576 | | | 330 | 177 | 425 |
| Aluminum | | | | | 118 | | | 229 | | | 110 | 46 | 132 |
| Calcium | | | | | 68 | | | 41 | | | 79 | 49 | 50 |
| Potassium | | | | | 3 | | | 16 | 5 | | | 28 | 14 |
| Magnesium | | | | | 7 | | | 2 | 9 | | | 6 | 5 |
| Sodium | | | | | 36 | | | 100 | 26 | | | 31 | 66 |
| Silicon | | | | | 6 | | | 9 | 5 | | | 8 | 10 |

| PROPERTY | | M | N | O | P | Q | R | S | T | U |
|---|---|---|---|---|---|---|---|---|---|---|
| Size (O.D.) | inches | 0.31 | 0.31 | 0.31 | 0.25 | 0.31 | 0.31 | 0.25 | 0.30 | 0.32 |
| Surface Area | m2g-1 | 0.67 | 1.28 | 1.09 | 1.74 | 1.12 | 1.12 | 1.13 | 1.99 | 0.50 |
| Water Pore Volume | % | 59.3 | 74.0 | 68.0 | 143.4 | 63.0 | 65.4 | 75.6 | 56.0 | 50.3 |
| Median Pore Diameter | microns | 2.6 | 1.6 | 2.2 | 2.1 | | | | 1.1 | |
| Residual Fluoride | % | 0.18 | 0.23 | 0.25 | 0.19 | 0 | 0 | 0.25 | 0.28 | 0 |
| Crush Strength | lbs | 8.3 | 5.2 | | 0.2 | | | | 12.4 | 13.0 |
| Water Leachables, ppm | | | | | | | | | | |
| Phosphate | | 0 | 14 | | 9 | | | | 0 | |
| Fluoride | | 202 | 311 | | 4 | | | | 198 | 0 |
| Aluminum | | 76 | 122 | | 88 | | | | 49 | |
| Calcium | | 9 | 23 | | 2 | | | | | |
| Potassium | | 6 | 6 | | 60 | | | | | 829 |
| Magnesium | | 2 | 8 | | 1 | | | | 1 | 20 |
| Sodium | | 27 | 37 | | 119 | | | | 70 | 1152 |
| Silicon | | 4 | 6 | | 157 | | | | 0 | |

Examples 1 to 78 relate to the performances of the foregoing catalysts.

TABLE 3

| Exp. No. | Cat. No. | # of Ag Impreg. | Support # | % Ag | % K | K Added How? | Conditions I | | Conditions II | | |
|---|---|---|---|---|---|---|---|---|---|---|---|
| | | | | | | | % EO | Eff | % EO | Eff | Day |
| 1 | 1 | 1 | A | 8 | 0.23 | Seq. | 0.9 | 88 | 0.17 | 67 | 20 |
| 2 | 2 | 1 | A | 18 | 0.40 | Co. | 1.6 | 90 | 0.16 | 67 | 26 |
| 3 | 3 | 1 | B | 20 | 0.08 | Co. | 1.6 | 86 | 0.40 | 78 | 23 |
| 4 | 4 | 3 | A | 35 | 0.33 | Seq. | 1.6 | 90 | 0.67 | 80 | 35 |
| 5 | 5 | 3 | A | 37 | 0.17 | Seq. | 1.5 | 88 | 0.83 | 82 | 48 |
| 6 | 6 | 4 | A | 46 | 0.14 | Seq. | 1.6 | 83 | 0.80 | 81 | 40 |

Conditions I: autoclave, 30% ethylene, 8% oxygen, 5 ppm ethylchloride, 5 ppm nitric oxide, 8000 GHSV and 240° C.
Conditions II: autoclave, 30% ethylene, 8% oxygen, 3% carbon dioxide, 0.3% ethane, 20 ppm ethylchloride, 15 ppm nitric oxide, 8000 GHSV and 270° C.

EXAMPLES 1-6

In Examples 1 through 6, catalyst nos. 1-6 are tested at the conditions noted in Table 3 to show the effect of different silver loadings on efficiency and activity. Table 3 shows that the catalysts made with the high silver loading, i.e., catalyst nos. 4, 5 and 6, are more active both initially and throughout the catalyst life than are catalysts 1, 2, and 3, the catalysts having lower silver loadings.

EXAMPLES 7-12

In Examples 7 through 12, the noted catalysts are tested showing the effect of sequential versus coincidental impregnation of potassium on high silver loaded catalysts. As shown in Table 4, higher initial efficiency occurs with those catalysts made by coimpregnation of potassium. After a period of time, however, the efficiencies of the catalysts made by the two procedures become approximately the same.

TABLE 4

| Exp. No. | Cat. No. | # of Ag Impreg. | Support # | % Ag | % K | K Added How? | Conditions I % EO | Eff. | Conditions II % EO | Eff. |
|---|---|---|---|---|---|---|---|---|---|---|
| 7 | 7 | 2 | C | 36.0 | 0.05 | Seq. | 1.69 (day 2) | 74.4 | 1.71 (day 9) | 74.6 |
| 8 | 8 | 2 | C | 38.5 | 0.10 | Co. | 1.82 (day 2) | 79.3 | 1.97 (day 9) | 75.7 |
| 9 | 9 | 2 | C | 38.5 | 0.10 | Seq. | 1.85 (day 1) | 82.0 | 2.00 (day 12) | 78.8 |
| 10 | 10 | 2 | C | 39.8 | 0.10 | Co. | 2.03 (day 1) | 88.0 | 2.07 (day 4) | 82.5 |
| 11 | 5 | 2 | A | 37.0 | 0.17 | Seq. | 1.54 (day 10) | 88.0 | 1.61 (day 13) | 82.7 |
| 12 | 11 | 2 | C | 39.3 | 0.15 | Co. | 2.12 (day 7) | 89.4 | 1.96 (day 9) | 84.2 |

Conditions I: autoclave, 30% ethylene, 8% oxygen, 5 ppm ethylchloride, 5 ppm nitric oxide, 8000 GHSV and 240° C.
Conditions II: autoclave, 30% ethylene, 8% oxygen, 3% carbon dioxide, 0.3% ethane, 20 ppm ethylchloride, 15 ppm nitric oxide, 8000 GHSV and 270° C.

EXAMPLES 13-15

In Examples 13 through 15, catalysts no. 12, 13 and 14 are tested in which the effect of rinsing freshly impregnated catalysts with ethylenediamine, particularly after (1) the first such impregnation and after (2) both the first and second impregnations. As shown in Table 5, washing of freshly impregnated catalysts before roasting strips off some of the excess occluding silver which helps prevent plugging of the support pores thereby increasing efficiency. The catalyst prepared with one rinse is 10% more active than the one which had no rinse. Rinsing after each impregnation resulted in a lower activity due to the removal of too much silver.

EXAMPLES 16-21

In Examples 16 through 21, catalysts are tested having high and low silver contents in autoclaves under both air and oxygen conditions.

As shown in Table 6, as expected, the catalysts run under air conditions are less active than those run in oxygen. This lower activity demands higher temperature operation to compensate for such activity decrease which, in turn, increases the rate of deactivation. High silver content catalysts, however, are shown to be more active than low silver content catalysts.

TABLE 6

| Exp. No. | Cat. No. | Support Number | % Ag | % K | Operating Conditions | Temp. °C. | % EO | Eff. |
|---|---|---|---|---|---|---|---|---|
| 16 | 15 | E | 18.0 | 0.09 | O2 | 240 | 1.1 | 90 |
| 17 | 15 | E | 18.0 | 0.09 | Air | 270 | 0.4 | 80 |
| 18 | 16 | F | 32.0 | 0.10 | O2 | 240 | 1.9 | 89 |
| 19 | 16 | F | 32.0 | 0.10 | Air | 270 | 0.9 | 79 |
| 20 | 17 | B | 20 | 0.05 | Air | 270 | 0.45 | 76 |
| 21 | 9 | C | 38.5 | 0.10 | Air | 270 | 0.90 | 79 |

O2 Conditions: autoclave, 30% ethylene, 8% oxygen, 5 ppm ethylchloride, 5 ppm nitric oxide, 8000 GHSV and 240° C.
Air Conditions: autoclave, 8% ethylene, 6% oxygen, 4% CO2, 0.3% ethane, 12 ppm ethylchloride, 8 ppm nitric oxide, 8000 GHSV and 270° C.

TABLE 5

| Exp. No. | Cat.* No. | Comment | % Ag | ppm K | % EO | % Eff | T (°C.) |
|---|---|---|---|---|---|---|---|
| 13 | 12 | No rinse | 39.2 | 978 | 1.30 | 85.1 | 236 |
| 14 | 13 | aft. 1'st Ag | 36.7 | 918 | 1.45 | 85.3 | 236 |
| 15 | 14 | aft 1 & 2 Ag | 34.9 | 830 | 1.10 | 84.7 | 236 |

Test Conditions: Autoclave, 30% ethylene, 8% Oxygen, 3.0% CO2, 7 ppm ECl, 10 ppm nitric oxide.
*The support for each of Catalysts 12, 13 and 14 is Support No. D.

EXAMPLES 22-27

In Examples 22 through 27, catalyst nos. 18 through 22 are tested showing the effect of silver loading, rubidium concentration and percentage carbon dioxide on these catalysts as shown in Table 7 below.

TABLE 7

| Exp. No. | Cat. No. | # of Ag Impreg. | Support # | % Ag | % Rb | Operating Conditions | Temp (°C.) | % EO | Eff. % |
|---|---|---|---|---|---|---|---|---|---|
| 22 | 18 | 1 | G | 19.7 | 0.20 | O2 (0% CO2) | 223 | 1.04 | 77.0 |
| 23 | 19 | 2 | G | 40.0 | 0.20 | O2 (0% CO2) | 218 | 1.51 | 80.0 |
| 24 | 20 | 2 | G | 39.9 | 0.30 | O2 (3% CO2) | 220 | 1.50 | 83.5 |
| 25 | 21 | 2 | H | 40.0 | 0.10 | O2 (0% CO2) | 220 | 1.30 | 87.0 |
| 26 | 21 | 2 | H | 40.0 | 0.10 | O2 (3% CO2) | 220 | 1.12 | 74.0 |
| 27 | 22 | 2 | H | 39.9 | 0.20 | O2 (3% CO2) | 220 | 1.95 | 80.0 |

Operating Conditions: Autoclave, 30% ethylene, 8% Oxygen, 5 ppm NO, 5 ppm ECl, 8000 GHSV.

EXAMPLES 28-31

In Examples 28 through 31, catalysts 23 and 24 are tested in which a comparison of high and low silver content catalysts in pilot plant use is made. The results are set forth in Table 8 below.

TABLE 8

| Exp. No. | Cat. No. | # of Ag Impreg. | Support # | % Ag | % K | Temp. °C. | Max Loading (#/cu. ft/hr.) | Eff. | Day |
|---|---|---|---|---|---|---|---|---|---|
| 28 | 23 | 1 | B | 20 | 0.06 | 250 | 7.9[1] | 88 | 20 |
| 29 | 23 | 1 | B | 20 | 0.06 | 260 | 2.0[2] | 88 | 42 |
| 30 | 24 | 2 | D | 40 | 0.10 | 243 | 9.8[3] | 87 | 20 |

TABLE 8-continued

| Exp. No. | Cat. No. | # of Ag Impreg. | Support # | % Ag | % K | Temp. °C. | Max Loading (#/cu. ft/hr.) | Eff. | Day |
|---|---|---|---|---|---|---|---|---|---|
| 31 | 24 | 2 | D | 40 | 0.10 | 258 | 9.3[4] | 86 | 39 |

Conditions:
[1] 1.0% EO, 7.5% $O_2$, 20% $C_2H_4$, 3.0% $CO_2$, 0.3% $C_2H_6$, 7.5 ppm ECl, 16 ppm NO, 275 psig, 6200 GHSV.
[2] 0.35% EO, 8.0% $O_2$, 24% $C_2H_4$, 1.0% $CO_2$, 0.2% $C_2H_6$, 23 ppm ECl, 20 ppm NO, 220 psig, 4700 GHSV.
[3] 2.22% EO, 8.5% $O_2$, 30.0% $C_2H_4$, 3.0% $CO_2$, 0.2% $C_2H_6$, 6 ppm ECl, 38 ppm NO, 300 psig, 3600 GHSV.
[4] 2.30% EO, 8.5% $O_2$, 28.0% $C_2H_4$, 5.0% $CO_2$, 0.2% $C_2H_6$, 14 ppm ECl, 52 ppm NO, 240 psig, 3300 GHSV.

EXAMPLES 32–34

In Examples 32 through 34, catalyst nos. 24, 25, and 26 are tested to show a comparison of pilot plant operation under both air and oxygen conditions as shown in Table 9.

TABLE 9

| Exp. No. | Cat. No. | Support # | % Ag | % K | Operating Conditions | Temp. °C. | Max Loading (#/cu. ft/hr.) | Eff. | Aging Rate (% EO/d) |
|---|---|---|---|---|---|---|---|---|---|
| 32 | 25 | I | 38 | 0.03 | Air | 265 | 12.0 | 82 | 0.09 |
| 33 | 24 | D | 40 | 0.10 | $O_2^1$ | 245 | 11.5 | 88 | 0.04 |
| 34 | 26 | D | 40 | 0.60 | $O_2^2$ | 220 | 9.2 | 89 | 0.01 |

Air conditions: 8% $O_2$, 12% $C_2H_4$, 2% $CO_2$, 0.6% $C_2H_6$, 15 ppm ECl, 15 ppm NO, 220 psig, 5300 GHSV.
$O_2^1$ conditions: 8.5% $O_2$, 30% $C_2H_4$, 3% $CO_2$, 0.2% $C_2H_6$, 40 ppm ECl, 40 ppm NO, 300 psig, 3600 GHSV.
$O_2^2$ conditions: 8.5% $O_2$, 30% $C_2H_4$, 0.5% $CO_2$, 0.3% $C_2H_6$, 9 ppm ECl, 6 ppm NO, 300 psig, 6600 GHSV.

EXAMPLES 35–42

In Examples 35 through 42, catalyst nos. 27 through 34 are tested to show a comparison of high and low silver content catalysts using an autoclave under air conditions, which catalysts contain supports having a platelet-type morphology and residual fluorine-containing substance(s). From Table 10, it is seen that those catalysts having silver concentrations of greater than about 30% by weight have improved stability and activity while maintaining high efficiency.

TABLE 10

| Exp. No. | Cat. No. | No. of Ag Impreg. | Support Number | % Ag | ppm Cs (ppm K) | Efficiency (1.4% EO) | Temperature °C. @ 1.4% EO |
|---|---|---|---|---|---|---|---|
| 35 | 27 | 1 | J | 19.9 | 544 | 76.6 | 270 |
| 36 | 28 | 2 | J | 31.8 | 554 | 77.0 | 254 |
| 37 | 29 | 1 | K | 19.9 | 723 | 75.0 | 270 |
| 38 | 30 | 2 | K | 33.0 | 842 | 75.5 | 254 |
| 39 | 31 | 1 | L | 20.4 | 687 | 76.9 | 270 |
| 40 | 32 | 2 | L | 33.7 | 709 | 76.9 | 251 |
| 41 | 33 | 1 | L | 20.7 | 709 (209) | 76.5 | 267 |
| 42 | 34 | 2 | L | 32.9 | 693 (203) | 76.0 | 262 |

Air conditions: 8% $C_2H_4$, 6% $O_2$, 6.5% $CO_2$, 0.5% $C_2H_6$, 15 ppm ethylchloride, 8000 GHSV, 275 psig.

EXAMPLES 43–46

In Examples 43 through 46, catalyst nos. 35 through 38 are tested having non-platelet type carriers with high surface area, showing the effect of high and low silver content, as set forth in Table 11.

TABLE 11

| Exp No. | Cat. No. | Support # | Cs (ppm) | % Ag | Method | 1.0% EO Temp. (°C.) | 1.0% EO % Eff | 1.4% EO Temp. (°C.) | 1.4% EO % Eff. |
|---|---|---|---|---|---|---|---|---|---|
| 43 | 35 | Q | 699 | 16.2 | 1 | 258 | 76.3 | 271 | 71.4 |
| 44 | 36 | R | 528 | 20.1 | 1 | 251 | 73.8 | 268 | 67.5 |
| 45 | 37 | R | 641 | 33.4 | 2 | 244 | 77.1 | 253 | 72.2 |
| 46 | 38 | R | 628 | 33.3 | 3 | 241 | 78.9 | 248 | 75.7 |

Method 1: Single, standard co-impregnation of silver and promoter.
Method 2: Two impregnations, 1st) standard with 50% of promoter, 2nd) pore volume (incipient wetness) method with 50% of promoter.
Method 3: Two standard impregnation, with 50% of the promoter added in each.
Test conditions: Standard Air-process conditions (6% $O_2$, 8% $C_2H_4$, 6.5% $CO_2$, 7.5 ppm ECl).
These catalysts have been prepared with a batch of $Cs_2SO_4$ which has been shown to provide 1-1.5% lower efficiencies due to $H^+$ impurity.

EXAMPLES 47–52

In Examples 47 through 52, catalyst nos. 39 and 40 are tested at various conditions and with high and low silver contents in a pilot plant. The results are shown in Table 12 where the catalysts having higher silver content have better activity.

TABLE 12

| Exp No. | Cat. No. | Number of Ag Impreg. | Support Number | % Ag | Operating Conditions | Eff. | Temp. °C. | Age Days |
|---|---|---|---|---|---|---|---|---|
| 47 | 39 | 2 | G | 31.7 | I | 81.0 | 217.0 | 17 |
| 48 | 39 | 2 | G | 31.7 | II | 80.0 | 228.0 | 46 |
| 49 | 39 | 2 | G | 31.7 | III | 80.3 | 235.4 | 28 |
| 50 | 40 | 1 | D | 20.2 | I | 83.4 | 229.4 | 14 |
| 51 | 40 | 1 | D | 20.2 | II | 81.7 | 239.7 | 41 |

TABLE 12-continued

| Exp No. | Cat. No. | Number of Ag Impreg. | Support Number | % Ag | Operating Conditions | Eff. | Temp. °C. | Age Days |
|---|---|---|---|---|---|---|---|---|
| 52 | 40 | 1 | D | 20.2 | III | 80.5 | 252.0 | 21 |

Operating Conditions:
I: 2.3% EO, 8.5% $O_2$, 30% $C_2H_4$, 5.0% $CO_2$, 0.1% $C_2H_6$, 6 ppm ECl, 240 psig, 3200 GHSV.
II: 2.5% EO, 8.5% $O_2$, 30% $C_2H_4$, 6.0% $CO_2$, 0.1% $C_2H_6$, 6.0 ppm ECl, 300 psig, 3600 GHSV.
III: 1.65% EO, 6.5% $O_2$, 10.0% $C_2H_4$, 6.0% $CO_2$, 0.1% $C_2H_6$, 4.0 ppm ECl, 300 psig, 5300 GHSV.

EXAMPLES 53–56

In Examples 53 through 56, catalyst nos. 41 through 44 are tested to show a comparison of molybdate-promoted catalysts prepared by co-impregnation and sequential impregnation of cesium molybdate. As shown in Table 13, it is desirable to add the molybdate with the silver via co-impregnation in order to obtain the desired efficiency promotion. Sequential addition of molybdate after silver deposition does not increase the efficiency as well.

TABLE 13

| Exp. No. | Cat. No. (Sup. No.) | Impreg. Method | % Ag | ppm Cs (MoO4) | Temp (°C.) | EO mole % | % Eff. | ECl |
|---|---|---|---|---|---|---|---|---|
| 53 | 41 (I) | Seq. | 16 | 520 | 230 | 0.45 | 80.4 | 2.0 |
| 54 | 42 (S) | Seq. | 18 | 517 | 230 | 0.46 | 80.7 | 1.5 |
| 55 | 43 (S) | Co-impreg | 15 | 500 | 230 | 0.56 | 83.2 | 2.5 |
| 56 | 44 (I) | Co-impreg | 30 | 500 | 230 | 0.47 | 84.5 | 4.5 |
|  |  |  |  |  | 254 | 1.01 | 78.5 | 1.6 |

Oxygen conditions: autoclave, 30% $C_2H_4$, 8% $O_2$, 0.5% $C_2H_6$, 0% $CO_2$, 275 psig, 8000 GHSV.

EXAMPLES 57–61

Examples 57 through 61 are related to Examples 53 through 56 in that comparisons are made of molybdate-promoted catalysts prepared by different silver impregnation techniques. In these examples, catalyst nos. 45–49 are prepared by adding the molybdate promoter with the second silver impregnation. As shown in Table 14, it is best to add the molybdate and sulfate promoters with as much silver as possible. That is, the second impregnating solution which contained the molybdate promoter desirably contained a higher concentration of silver than the first impregnating solution.

TABLE 14

| Exp No. | Cat. No. | Total Ag wt. % | Ag wt. % Added 1st Impreg. | Ag wt. % Added 2nd Impreg. | Cs* ppm | Rb* ppm | Temp. °C. | EO mole % | % Eff. |
|---|---|---|---|---|---|---|---|---|---|
| 57 | 45 | 20 | 10 | 10 | 500 | 200 | 254 | 1.25 | 80.6 |
| 58 | 46 | 20 | 0 | 20 | 500 | 200 | 247 | 1.25 | 82.3 |
| 59 | 47 | 30 | 20 | 10 | 550 | 220 | 254 | 1.25 | 79.4 |
| 60 | 48 | 30 | 10 | 20 | 550 | 220 | 243 | 1.25 | 83.4 |
| 61 | 49 | 40 | 20 | 20 | 550 | 220 | 232 | 1.25 | 81.6 |

Oxygen conditions: autoclave, 30% $C_2H_4$, 8% $O_2$, 0.5% $C_2H_6$, 6.5% $CO_2$, 2 ppm ECl, 275 psig, 8000 GHSV.
*40% of the anions were added as molybdate and rest as sulfate.
All catalysts supported on Support No. L

EXAMPLES 62–64

In Examples 62 through 64, catalyst nos. 50 through 52, respectively, are tested at high silver content on a carrier having 2 m²/g. The results are set forth in Table 15.

TABLE 15

| Exp. No. | Cat. No. | Total Ag wt. % | Surface Area of Support $m^2g^{-1}$ | Cs ppm (MoO4) | Cs ppm (SO4=) | Temp. °C. | EO mole % | % Eff. |
|---|---|---|---|---|---|---|---|---|
| 62 | 50 | 30 | 2 | 400 | 1200 | 247 | 1.25 | 79.2 |
| 63 | 51 | 40 | 2 | 0 | 1200 | 219 | 1.25 | 81.2 |
| 64 | 52 | 40 | 2 | 400 | 1200 | 243 | 1.25 | 83.5 |

Oxygen conditions: autoclave, 30% $C_2H_4$, 8% $O_2$, 0.5% $C_2H_6$, 6.5% $CO_2$, 2 ppm ECl, 275 psig, 8000 GHSV.
The support for each catalyst is Support No. T.

EXAMPLES 65–67

In Examples 65 through 67, the effect of promoter level on high silver-containing catalyst is demonstrated as set forth in Table 16.

TABLE 16

| Exp. No. | Cat. No. | Total Ag wt. % | Surface Area of Support $m^2g^{-1}$ | Cs ppm (MoO4) | Cs ppm (SO4=) | Temp. °C. | EO Mole % | % Eff. |
|---|---|---|---|---|---|---|---|---|
| 65 | 53 | 30 | 1.1 | 0 | 750 | 228 | 1.25 | 81.6 |
| 66 | 54 | 30 | 1.1 | 50 | 700 | 227 | 1.25 | 82.3 |

TABLE 16-continued

| Exp. No. | Cat. No. | Total Ag wt. % | Surface Area of Support $m^2g^{-1}$ | Cs ppm (MoO4) | Cs ppm (SO4=) | Temp. °C. | EO Mole % | % Eff. |
|---|---|---|---|---|---|---|---|---|
| 67 | 55 | 30 | 1.1 | 100 | 750 | 236 | 1.25 | 83.5 |

Oxygen conditions: autoclave. 30% $C_2H_4$, 8% $O_2$, 0.5% $C_2H_6$, 6.5% $CO_2$, 2 ppm ECl, 275 psig, 8000 GHSV. The support for these catalysts is Support No. D.

EXAMPLES 68-77

| Exp. No. | Cat. No. | Ag, wt. % | Support No. | Surface Area $M^2/g$ | Decrease in Temperature, °C. At Day 4 | Delta Efficiency (%) At Day 4 |
|---|---|---|---|---|---|---|
| 68 | 56 | 33 | M | 0.67 | 4.5 | 0 |
| 69* | 57 | 20 | M | 0.67 | — | — |
| 70 | 58 | 33.6 | N | 1.28 | 7 | 0 |
| 71* | 59 | 19.5 | N | 1.28 | — | — |
| 72* | 60 | 20.4 | O | 1.09 | — | — |
| 73 | 61 | 32.5 | O | 1.09 | 10 | +1 |
| 74 | 62 | 33 | K | 1.51 | 14 | +1 |
| 75* | 63 | 19.9 | K | 1.51 | — | — |
| 76* | 64 | 15.5 | P | 1.74 | — | — |
| 77 | 65 | 40.6 | P | 1.74 | 20 | +2 |

These examples demonstrate that high silver-content catalysts offer increased activity and efficiency depending upon the properties of the support. As can be seen, as the surface area of the support increases, there is an increase in activity for the high silver-content catalyst as seen by the decrease in operating temperature required to obtain a constant 1.4% of ethylene oxide production.

EXAMPLE 78

In this example, a comparison is made to show the effect of high silver content on a support having a low surface area, i.e., a surface area below that required by the present invention.

In particular, a low silver-content (15% silver by weight of finished cataylst), cesium and potassium sulfate promoted catalyst having a low surface area and a low porosity carrier (Support No. U) was prepared. This catalyst is tested under oxygen conditions at two different levels of gas flow rate. The processing conditions included 30% $C_2H_4$, 8% $O_2$, 6.5% $CO_2$, 0.5% $C_2H_6$, and 10 ppm ECl). A gas hourly space velocity (GHSV) of 4000 $H^{-1}$ was used for the first run followed by a GHSV of 8000 $H^{-1}$ for the second run. The effect of doubling the space velocity at constant production (i.e., outlet EO) is the same as doubling the rate (i.e., turnover frequency) of the catalyst. This is tantamount to halving the silver surface area on the catalyst support.

The results of this study show that adding a high silver content to a low surface area support would be expected to have very little benefit on the efficiency of the catalyst. The specific results are set forth in Table 17 below.

TABLE 17

| EO | Eff. @ 4000 GHSV | Eff. @ 8000 GHSV |
|---|---|---|
| 0.5 | 80.9 | — |
| 1.0 | 80.4 | 80.3 |
| 2.0 | 77.6 | 76.7 |

CARRIER DESCRIPTIONS

The properties listed for each carrier for the following examples are measured with procedures described above.

CARRIER "AA"

Carrier AA is an alpha alumina carrier with properties:

| Surface Area | 1.17 $M^2/g$ |
|---|---|
| Water pore volume | 0.65 cc/g |
| Crush strength, FPCS | 7.1 lbs. |
| Total pore volume, Hg | 0.70 cc/g |
| Packing density | 34.2 lbs/ft$^3$ |

PORE SIZE DISTRIBUTION, % TOTAL PORE VOLUME

| Pore Size Microns | % Total Pore Volume |
|---|---|
| P1 (<0.1) | 1.0 |
| P2 (0.1–0.5) | 10.5 |
| P3 (0.5–1.0) | 11.5 |
| P4 (1.0–10.0) | 22.0 |
| P5 (10.0–100) | 42.0 |
| P6 (>100) | 13.0 |

ACID LEACHABLE IMPURITIES 378 ppm sodium, and 330 ppm potassium

WATER LEACHABLE IMPURITIES 9 ppm phosphate, 4 ppm fluoride, 88 ppm aluminum, 2 ppm calcium, 60 ppm potassium, 1 ppm magnesium, 119 ppm sodium, and 157 ppm silicon.

SURFACE ACIDITY

The acidity of carrier AA is 0.45 micromoles $NH_3/g$ carrier.

CARRIER "AB"

Carrier AB is an alpha alumina carrier with properties:

| Surface Area | 0.48 M²/g |
|---|---|
| Water Pore Volume | 0.50 cc/g |
| Crush Strength, FPCS | 17.4 lbs. |
| Total Pore Volume, Hg | 0.53 cc/g |

PORE SIZE DISTRIBUTION/% TOTAL PORE VOLUME

| Pore Size Microns | % Total Pore Volume |
|---|---|
| P1 (<0.1) | 0.5 |
| P2 (0.1-0.5) | 3.0 |
| P3 (0.5-1.0) | 10.5 |
| P4 (1.0-10.0) | 29.0 |
| P5 (10.0-100) | 46.0 |
| P6 (>100) | 11.0 |

ACID LEACHABLE IMPURITIES 1240 ppm sodium, and 954 ppm potassium.

SURFACE ACIDITY 0.11 Micromoles $NH_3$/g carrier.

CARRIER "AC"

Carrier AC is an alpha alumina carrier (available from the Norton Company, Stow, Ohio, as 5502) with properties:

| Surface Area | 0.80 M²/g |
|---|---|
| Water Pore Volume | 0.26-0.32 cc/g |
| Crush Strength, FPCS | 20 lbs. |
| Total Pore Volume, Hg | 0.25-0.34 cc/g |

PORE SIZE DISTRIBUTION/% TOTAL PORE VOLUME

| Pore Size Microns | % Total Pore Volume |
|---|---|
| P1 (<0.1) | 0 |
| P2 (0.1-0.5) | 10.0 |
| P3 (0.5-1.0) | 28.0 |
| P4 (1.0-10.0) | 54.0 |
| P5 (10.0-100) | 6.0 |
| P6 (>100) | 2.0 |

CHEMICAL ANALYSIS

| Alumina ($Al_2O_3$) | 99.6% | CaO | 0.1% |
|---|---|---|---|
| $SiO_2$ | <0.05% | MgO | <0.02% |
| $Fe_2O_3$ | <0.1% | $Na_2O$ | 0.2% |
| $TiO_2$ | <0.01% | $K_2O$ | <0.02% |
| MnO | <0.01% | | |

SURFACE ACIDITY 1.20 Micromoles $NH_3$/g carrier.

CARRIER "AD"

Carrier AD is an alpha alumina carrier with properties:

| Surface Area | 0.71 M²/g |
|---|---|
| Water Pore Volume | 0.45 cc/g |
| Crush Strength, FPCS | 26.0 lbs. |
| Total Pore Volume, Hg | 0.48 cc/g |

PORE SIZE DISTRIBUTION/% TOTAL PORE VOLUME

| Pore Size Microns | % Total Pore Volume |
|---|---|
| P1 (<0.1) | 5.3 |
| P2 (0.1-0.5) | 4.2 |
| P3 (0.5-1.0) | 25.3 |
| P4 (1.0-10.0) | 28.4 |
| P5 (10.0-100) | 36.8 |
| P6 (>100) | 0 |

CARRIER "AE"

Carrier AE is an alpha alumina carrier with properties:

| Surface Area | 2.97 M²/g |
|---|---|
| Total Pore Volume, Hg | 0.58 cc/g |

PORE SIZE DISTRIBUTION/% TOTAL PORE VOLUME

| Pore Size Microns | % Total Pore Volume |
|---|---|
| P1 (<0.1) | 0 |
| P2 (0.1-0.5) | 32.2 |
| P3 (0.5-1.0) | 32.3 |
| P4 (1.0-10.0) | 33.9 |
| P5 (10.0-100) | 1.6 |
| P6 (>100) | 0 |

CHEMICAL PURITY (TRACE ANALYSIS)

400 ppm Si, 240 ppm Fe, 50 ppm Ti, and 120 ppm Ga.

CARRIER "AF"

Carrier AF is an alpha alumina carrier with properties:

| Surface Area | 3.3 M²/g |
|---|---|
| Total Pore Volume, Hg | 0.56 cc/g |
| Median Pore Diameter | 0.41 micron |

CHEMICAL PURITY (TRACE ANALYSIS)

180 ppm Fe, 30-50 ppm Si, 34 ppm Ti, and 100 ppm Ga.

CARRIER "AG"

Carrier AG is an alpha alumina carrier with properties:

| Surface Area | 2.3 M²/g |
|---|---|
| Total Pore Volume, Hg | 0.27 cc/g |
| Median Pore Diameter | 0.30 micron |

PORE SIZE DISTRIBUTION/% TOTAL PORE VOLUME

| Pore Size Microns | % Total Pore Volume |
|---|---|
| P1 (<0.1) | 4.0 |
| P2 (0.1–0.5) | 96.0 |
| P3 (0.5–1.0) | 0 |
| P4 (1.0–10.0) | 0 |
| P5 (10.0–100) | 0 |
| P6 (>100) | 0 |

TRACE ANALYSIS 230 ppm Fe, 100–150 ppm Si, 9 ppm Ti, and 60 ppm Ga.

CARRIER "AH"

Carrier AH is an alpha alumina carrier with properties:

| | |
|---|---|
| Surface Area | 1.58 $M^2/g$ |
| Water Pore Volume | 0.66 cc/g |
| Crush Strength, FPCS | 8.5 lbs. |
| Total Pore Volume, Hg | 0.674 cc/g |
| Packing Density | 34.9 lbs/ft$^3$ |
| Median Pore Diameter | 2.2 microns |

PORE SIZE DISTRIBUTION/% TOTAL PORE VOLUME

| Pore Size Microns | % Total Pore Volume |
|---|---|
| P1 (<0.1) | 0.5 |
| P2 (0.1–0.5) | 11.0 |
| P3 (0.5–1.0) | 21.0 |
| P4 (1.0–10.0) | 25.0 |
| P5 (10.0–100) | 29.0 |
| P6 (>100) | 14.0 |

ACID LEACHABLE IMPURITIES 1020 ppm Na, 564 ppm K, 313 ppm Ca and 1936 ppm Al.

CARRIER "AI"

Carrier AI is an alpha alumina carrier with properties:

| | |
|---|---|
| Surface Area | 1.79 $M^2/g$ |
| Water Pore Volume | 0.67 cc/g |
| Crush Strength, FPCS | 8.2 lbs. |
| Total Pore Volume, Hg | 0.70 cc/g |
| Packing Density | 34.9 lbs/ft$^3$ |
| Median Pore Diameter | 1.4 microns |

PORE SIZE DISTRIBUTION/% TOTAL PORE VOLUME

| Pore Size Microns | % Total Pore Volume |
|---|---|
| P1 (<0.1) | 0 |
| P2 (0.1–0.5) | 12.0 |
| P3 (0.5–1.0) | 25.0 |
| P4 (1.0–10.0) | 33.0 |
| P5 (10.0–100) | 21.0 |
| P6 (>100) | 9.0 |

ACID LEACHABLE IMPURITIES 1074 ppm Na, 542 ppm K, 233 ppm Ca and 1986 ppm Al.

CARRIER "AJ" (IDENTICAL TO CARRIER R)

Carrier AJ is carrier AA which has been washed according to the following procedure: 30 minutes in boiling water, and 6 times washed (rinsed) at 25° C. each times 1000 cc carrier is washed with 1200 cc water. The carrier is dried at 300° C.

WATER LEACHABLE IMPURITIES 1 ppm fluoride, 2 ppm phosphate, 59 ppm aluminum, 8 ppm calcium, 61 ppm potassium, 4 ppm magnesium, 51 ppm sodium and 144 ppm silicon.

Acidity of Carrier AJ is 1.03 micromoles of ammonia per gram of carrier.

CARRIER "AK"

Carrier AK is an alpha alumina carrier with properties:

| | |
|---|---|
| Surface Area | 0.91 $m^2/g$ |
| Water pore volume | 0.49 cc/g |
| Crush Strength, fpcs | 13 lbs. |
| Total pore volume, Hg | 0.51 cc/g |
| Packing Density | 41.6 lbs/ft$^3$ |

PORE SIZE DISTRIBUTION/% TOTAL PORE VOLUME

| Pore Size Micron | Total Pore Volume, % |
|---|---|
| P1 (<0.1) | 1.0 |
| P2 (0.1–0.5) | 9.5 |
| P3 (0.5–1.0) | 17.0 |
| P4 (1.0–10.0) | 19.0 |
| P5 (10.0–100) | 45.5 |
| P6 (>100) | 8.0 |

WATER LEACHABLE IMPURITIES 25 ppm phosphate, 1 ppm fluoride, 170 ppm aluminum, 9 ppm calcium, 84 ppm potassium, 1 ppm magnesium, 188 ppm sodium, and 240 ppm silicon.

EXAMPLES 79 AND 80 (BOTH COMPARATIVE)

The catalysts are prepared using the general procedures set forth below.

IMPREGNATION SOLUTION PREPARATION

1. About 118 grams of ethylenediamine (high purity grade) are mixed with 200 grams of distilled water.

2. About 123 grams of oxalic acid (oxalic acid dihydrate, reagent grade) are slowly added to the aqueous ethylenediamine solution at ambient conditions. An exothermic reaction occurs and the solution temperature rises to about 40° C.

3. About 216 grams of silver oxide powder are then added slowly to the solution of step 2 while continuing to stir.

4. To the solution in 3 above is added about 43 grams of monoethanolamine (Fe and Cl free). (Note: steps 1 to 4 are performed in a batch 2 times the size set forth herein and then divided into two equal aliquots.)

5. To the first aliquot is added 7.91 grams of a standard cesium hydroxide solution containing 0.010371 gram of Cs per gram of solution (prepared by dissolving CsOH in distilled water), and 8.02 grams of a potassium carbonate standard solution (containing 0.003031 gram of K per gram of solution). An additional 5.03 grams of distilled water are added. Total solution weight is 371.06 grams at 250 ml volume.

To the second aliquot is added 3.96 grams of the above cesium hydroxide standard solution and 4.01 grams of the above potassium carbonate solution. An additional 13.43 grams of distilled water are added. Total solution weight is 371.50 grams at 250 ml volume.

IMPREGNATION OF CARRIER

1. Two separate batches (200 grams each) of carrier AC are evacuated (about 2 inches Hg absolute) at room temperature. These two batches are impregnated with the first (catalyst 66) and second (catalyst 67) aliquots of solutions from 5 above respectively under vacuum for 1 hour each.
2. The excess solution is drained off for 30 minutes.

CATALYST ROASTING

1. Each batch of the impregnated carrier is roasted in hot air using a belt roaster at about 500° C. for 2.5 minutes. Air flow is 66.5 SCFH/in.$^2$.

A summary of Examples 79 and 80 is provided in Table 18. The catalyst is evaluated using an autoclave under Standard Conditions, Air Process, as described above.

Conditions and Example 84 is conducted under Oxygen Conditions.

TABLE 19

|  | STOCK SOLUTION | | |
| --- | --- | --- | --- |
|  | 1 | 2 | 3 |
| Ethylenediamine (grams) | 1112.05 | 858.40 | 275.05 |
| Oxalic Acid-dihydrate (gram) | 1112.14 | 860.00 | 272.88 |
| Silver Oxide (gram) | 1950.35 | 1506.00 | 482.40 |
| Monoethanolamine (gram) | 410.08 | 301.00 | 108.00 |
| Distilled Water (grams) | 2575.38 | 962.00 | 275.06 |

TABLE 20

|  | Catalyst | | |
| --- | --- | --- | --- |
|  | I | II | III |
| First Impregnation: | | | |
| Stock Solution No. | 1 | 2 | 3 |
| Solution Wt. used (grams) | 272.70 | 272.03 | 773.05 |
| Promoter Added (grams) | 0 | 0 | 0 |
| Support Wt. (grams) | 135.31 | 135.29 | 270.61 |
| Vacuum (inches) | 30 | 30 | 30 |
| Evacuation Time (min.) | 15 | 15 | 15 |
| Impregnation Time (min.) | 30 | 30 | 30 |
| Drain Time (min.) | 15 | 15 | 20 |
| Silver Pick up (wt. %) | 8.97 | 9.09 | 11.61 |
| Promoter Pick up (ppm) | 0 | 0 | 0 |
| Second Impregnation: | | | |
| Stock Solution No. | 2 | 2 | 3 |
| Solution wt. used (grams) | 240.99 | 189.02 | 638.60$^{a)}$ |
| Promoter Added (grams) | 0.8677, Cs$_2$SO$_4$ | 0.5238, Cs$_2$SO$_4$ | 1.0884, Cs$_2$SO$_4$ |
| Vacuum (inches) | 30 | 30 | 30 |
| Evacuation Time (min.) | 15 | 15 | 20 |
| Impregnation Time (min.) | 30 | 30 | 30 |
| Drain Time (min.) | 15 | 15 | 20 |
| Silver Pick up (wt. %) | 9.07 | 9.27 | 8.68 |
| Total Pick up: | | | |
| Silver (wt. %) | 18.04 | 18.36 | 20.29 |
| Promoter (ppm) | 845, Cs | 665, Cs | 386, Cs |

$^{a)}$Excess solution drained from the first impregnation was used.

TABLE 18

| | | | | | WT. PPM | | | | |
| --- | --- | --- | --- | --- | --- | --- | --- | --- | --- |
| EXAMPLE | CATALYST | CARRIER | NO OF IMPREGNATIONS | Ag WT. % | Cs AS CsOH | K AS K$_2$CO$_3$ | % EO | % EFF | TEMP (°C.) |
| 79 | 66 | AC | 1 | 10.42 | 75 | 25 | 1.00 | 69.5 | 251 |
| 80 | 67 | AC | 1 | 10.38 | 38 | 13 | 1.00 | 67.5 | 256 |

The following examples use substantially the procedures set forth for examples 79 and 80 except where otherwise indicated.

EXAMPLES 81 TO 84 (ALL COMPARATIVE)

Catalysts I, II and III are prepared according to the general procedure described in Examples 79 and 80. Three impregnation solutions (stock solutions) are prepared to be used for preparation of these catalysts. The detail data of each stock solution is provided in Table 19. Table 20 summarizes the preparation of the catalysts.

The performance of the catalysts is summarized in Table 21. Examples 81 to 83 are conducted under Air

EXAMPLES 85 AND 86 (BOTH COMPARATIVE)

Catalysts IV and V are made using a preparation procedure similar in functional aspects to catalysts in Examples 79 and 80. The summary of catalysts and test data is given in Table 22.

TABLE 21

| | | | | | WT. PPM | | | |
| --- | --- | --- | --- | --- | --- | --- | --- | --- |
| EXAMPLE | CATALYST | CARRIER | NO OF IMPREGNATIONS | Ag WT. % | Cs AS Cs$_2$SO$_4$ | % EO | % EFF | TEMP (°C.) |
| 81 | I | AC | 2 | 18.04 | 845 | 0.12 | 57.5 | 287 |
| | | | | | | (1.40)* | (48.7)* | (316)* |
| 82 | II | AC | 2 | 18.36 | 665 | 0.13 | 56.1 | 287 |
| | | | | | | (1.40)* | (47.4)* | (316)* |
| 83 | III | AC | 2 | 20.29 | 386 | 0.97 | 61.0 | 288 |
| | | | | | | (1.40)* | (56.7)* | (302)* |
| 84 | III | AC | 2 | 20.29 | 386 | 1.00 | 74.2 | 257 |

*Numbers in paranthesis are calculated from extrapolation of experimental data for comparison with other catalysts.

TABLE 22

| EXAMPLE | CATALYST | CARRIER | NO OF IMPREGNATIONS | Ag WT. %* | WT. PPM* Cs AS Cs₂SO₄ | WT. PPM* K AS K₂SO₄ | % EO | % EFF | TEMP (°C.) | CONDITION |
|---|---|---|---|---|---|---|---|---|---|---|
| 85 | IV | AB | 1 | 14.91 | 265 | 78 | 1.40 | 74.9 | 268 | Air |
| 86 | V | AB | 1 | 15.43 | 279 | 82 | 1.00 | 80.38 | 245 | O₂ |

*analyzed values

EXAMPLES 87 AND 88 (BOTH COMPARATIVE)

A stock solution IV is prepared with following ingredients:

| | |
|---|---|
| Ethylene diamine: | 1445.6 grams |
| Oxalic Acid dihydrate: | 1445.6 grams |
| Silver Oxide: | 2535.0 grams |
| Monoethanolamine: | 533.0 grams |
| Distilled Water: | 3348.8 grams |

Catalyst VI is prepared with impregnating 83.38 grams of carrier AB with a 272.44 grams aliquot of stock solution IV. The carrier is evacuated for 15 minutes and impregnation time is 30 minutes followed by 15 minute draining. The catalyst is roasted at 500° C. for 2.5 minutes on a belt roaster with 66 SCFH per square inch of air flow. The silver pick up is 15.43 wt. %. This roasted catalyst is impregnated for a second time with the drained solution (207.01 grams) from the first impregnation to which are added 2.8509 grams of an aqueous cesium sulfate solution containing 0.0383 gram of cesium per gram of solution. The impregnation procedure and roasting is identical to the first impregnation step. The silver pick up in second impregnation is 11.07 wt. %. The total pick up is 26.50 wt. % silver and 275 ppm cesium.

The summary of catalyst VI and its performance is given in Table 23.

TABLE 23

| EXAMPLE | CARRIER | NO OF IMPREGNATIONS | Ag WT. % | WT. PPM Cs AS Cs₂SO₄ | % EO | % EFF | TEMP (°C.) | CONDITION |
|---|---|---|---|---|---|---|---|---|
| 87 | AB | 2 | 26.5 | 275 | 1.40 | 75.20 | 262 | Air |
| 88 | AB | 2 | 26.5 | 275 | 1.00 | 80.67 | 235 | O₂ |

EXAMPLES 89 AND 90 (BOTH COMPARATIVE)

Catalysts VII and VIII are prepared by re-impregnating two small batches of catalyst IV of Example 85 for the second time according to the following procedure:

Catalyst VII: 80.06 grams of catalyst IV are evacuated for 15 minutes to 28 inches of Hg vacuum followed by 30 minutes impregnation with a solution prepared as follows:

| | |
|---|---|
| Ethylenediamine: | 36.16 grams |
| Oxalic Acid dihydrate: | 35.85 grams |
| Silver Oxide: | 59.00 grams |
| Monoethanolamine: | 13.36 grams |
| Distilled Water: | 47.00 grams |
| Promoter Standard Solution: (0.035 grams Cs as Cs₂SO₄/gram solution) | 2.30 grams |

The impregnated catalyst is drained for 30 minutes and roasted at 500° C. for 2.5 minutes on a belt roaster (66 SCFH/in² air flow). The total silver and cesium pick ups are: 27.58 wt. % Ag and 432 ppm Cs.

Catalyst VIII: An impregnation solution is prepared as follows:

| | |
|---|---|
| Ethylenediamine: | 30.58 grams |
| Oxalic Acid dihydrate: | 30.86 grams |
| Silver Oxide: | 54.10 grams |
| Monoethanolamine: | 11.57 grams |
| Distilled Water: | 57.00 grams |
| Promoter Standard Solution: (0.035 grams Cs as Cs₂SO₄/gram solution) | 1.75 grams |

86.50 grams of catalyst IV are impregnated for second time according to the procedure described for catalyst VII above. The total silver and cesium pick ups are: 26.68 wt. % Ag and 405 ppm Cs.

A summary of the catalysts and performance is provided in Table 24.

TABLE 24

| EXAMPLE | CATALYST | CARRIER | NO OF IMPREGNATIONS | Ag* WT. % | WT. PPM* Cs AS Cs₂SO₄ | WT. PPM* K AS K₂SO₄ | % EO | % EFF | TEMP (°C.) | CONDITION |
|---|---|---|---|---|---|---|---|---|---|---|
| 89 | VII | AB | 2 | 27.58 | 432 | 78 | 1.40 | 74.6 | 265 | Air |
| 90 | VIII | AB | 2 | 26.68 | 405 | 78 | 1.40 | 75.0 | 270 | Air |

*analyzed values

EXAMPLE 91 (COMPARATIVE)

Catalyst IX is prepared using the following impregnation solution:

| | |
|---|---|
| Ethylenediamine: | 36.07 grams |
| Oxalic Acid dihydrate: | 36.13 grams |
| Silver Oxide: | 63.27 grams |
| Monoethanolamine: | 12.66 grams |
| Distilled Water: | 56.15 grams |
| Promoter Standard Solution: (0.015 grams Cs as Cs₂SO₄/gram solution) | 13.22 grams |

69.21 grams of carrier AD are evacuated (28") for 15 minutes followed by impregnation with the above solution for 1 hour. The impregnated carrier is drained for 15 minutes and roasted at 500° C. for 2.5 minutes on a belt roaster with 66 SCFH/in² air. The silver pick up is 16.23 wt. % and the promoter pick up is 546 ppm cesium.

The catalyst and its performance is summarized in Table 25.

TABLE 25

| EX-AMPLE | CARRIER | Ag WT. % | WT. PPM Cs AS Cs$_2$SO$_4$ | % EO | % EFF | TEMP (°C.) | CONDITION |
|---|---|---|---|---|---|---|---|
| 91 | AD | 16.23 | 546 | 1.40 | 75.7-74.0[a] | 270-274[a] | Air |

[a]Both efficiency and temperature changed during approximately one week of testing. The efficiency declined while temperature increased.

EXAMPLES 92 AND 93

To a 125 ml aliquot of a solution containing 25.85 weight percent silver, 15.53 weight percent ethylene diamine, 15.53 weight percent oxalic acid-dihydrate, 5.73 weight percent monoethanol amine and 35.97 weight percent distilled water, is added 5.64 grams of a cesium sulfate solution containing 0.015 gram of cesium per gram of solution. A 69.28 grams batch of carrier AD is evacuated 30 minutes to 28 inches Hg vacuum and then impregnated with 125 milliliters of the above solution for 1 hour. The wet catalyst is drained for 30 minutes and roasted at 500° C. for 2.5 minutes on a belt roaster with 66.5 SCFH/in² air. The silver pick up is 15.51 wt. % and the promoter pick up is 288 ppm cesium. After maintaining 6.62 grams of this catalyst for analysis, the remainder is impregnated a second time with another 125 milliliters aliquot of the above solution to which 7.33 grams of the same cesium sulfate solution are added. The impregnation and roasting procedures are substantially identical to those for the first impregnation step. The total silver pick up is 25.85 wt. % and the total promoter pick up is 530 ppm cesium.

The catalyst and performance are summarized in Table 26.

TABLE 26

| EX-AMPLE | Ag WT. % | WT. PPM Cs AS Cs$_2$SO$_4$ | % EO | % EFF | TEMP (°C.) | CONDITION |
|---|---|---|---|---|---|---|
| 92 | 25.85 | 530 | 1.40 | 75.50 | 254 | Air |
| 93 | 25.85 | 530 | 1.00 | 81.50 | 230 | O$_2$ |

EXAMPLES 94 TO 99

Two stock solutions are used to prepare catalysts for these examples. One is stock solution No. IV as described in Examples 87 and 88. The other stock solution is No. V and is prepared as follows:

| | |
|---|---|
| Ethylenediamine: | 1112.00 grams |
| Oxalic Acid dihydrate: | 1112.00 grams |
| Silver Oxide: | 1950.00 grams |
| Monoethanolamine: | 410.00 grams |
| Distilled Water: | 2576.00 grams |

Catalysts X, XI, XII, XIII, XIV are prepared with carrier AE with similar procedures used in Examples 79 and 80. A summary of the preparation data are given in Table 27 and the performance data are given in Table 28.

TABLE 27

| | Catalyst | | | | |
|---|---|---|---|---|---|
| | X | XI | XII | XIII | XIV |
| First Impregnation: | | | | | |
| Stock Solution No. | V | V | V | V | IV |
| Solution Wt. used (grams) | 56.81 | 57.11 | 56.58 | 113.48 | 174.87 |
| Promoter Added (grams)* | 0.0765 as Cs$_2$SO$_4$ | 0.0540 | 0.0986 | 0.1516 | 0 |
| Support Wt. (grams) | 14.33 | 14.53 | 14.40 | 28.83 | 23.19 |
| Vacuum (inches) | 28 | 28 | 28 | 28 | 28 |
| Evacuation Time (min.) | 15 | 15 | 15 | 15 | 15 |
| Impregnation Time (min.) | 30 | 30 | 30 | 30 | 30 |
| Drain Time (min.) | 15 | 15 | 15 | 15 | 15 |
| Silver Pick up (wt. %) | 19.22 | 18.90 | 18.92 | 19.31 | 19.49 |
| Promoter Pick up (ppm) | 1020, Cs | 705, Cs | 1299, Cs | 1017, Cs | 0 |
| Second Impregnation: | | | | | |
| Stock Solution No. | | | | | IV |
| Solution wt. used (grams) | | | | | 148.34[a] |
| Promoter Added (grams)* | | | | | 0.2274/ Cs$_2$SO$_4$ |
| Vacuum (inches) | | | | | 28 |
| Evacuation Time (min.) | | | | | 15 |
| Impregnation Time (min.) | | | | | 30 |
| Drain Time (min.) | | | | | 15 |
| Silver Pick up (wt. %) | | | | | 11.86 |
| Total Pick up: | | | | | |
| Silver (wt. %) | 19.22 | 18.90 | 18.92 | 19.31 | 31.35 |
| Promoter (ppm) | 1020, Cs | 705, Cs | 1299, Cs | 1017, Cs | 901, Cs |

[a]Excess solution drained from the first impregnation is used.
*Added as aqueous solution containing 0.0383 gram of cesium per gram of solution.

TABLE 28

| EX-AMPLE | CATA-LYST | CARRIER | Ag WT. % | WT. PPM Cs AS Cs$_2$SO$_4$ | % EO | % EFF | TEMP (°C.) | CONDI-TION |
|---|---|---|---|---|---|---|---|---|
| 94[a] | X | AE | 19.22 | 1020 | 1.40 | 82.4 | 238 | O$_2$ |
| 95[a] | XI | AE | 18.90 | 705 | 1.43 | 78.6 | 239 | O$_2$ |
| 96[a] | XII | AE | 18.92 | 1299 | 1.45 | 81.4 | 239 | O$_2$ |
| 97 | XIII | AE | 19.31 | 1017 | 0.60 (1.40)* | 72.6 (64.6)* | 247 (268)* | Air |
| 98 | XIV | AE | 31.35 | 901 | 1.00 (1.40)* | 70.6 (66.6)* | 246 (256)* | Air |
| 99[a,c] | IV | AB | 14.91 | 265[b] | 1.45 | 81.0 | 233 | O$_2$ |

[a]Micro-Reactors - The amount of catalyst used is 1 cc 14/30 mesh size - total pressure is 150 psig and GHSV = 6000 hr$^{-1}$. The microreactor used in the examples herein is a tube with a ¼ inch diameter.
[b]Also contains 78 ppm K as K$_2$SO$_4$.
[c]Comparative
*Numbers in parenthesis are calculated from extrapolation of experimental data for comparison with other catalysts.

EXAMPLES 100 AND 101

An impregnation solution with following composition is prepared:

| | |
|---|---|
| Ethylenediamine: | 111.20 grams |
| Oxalic Acid dihydrate: | 111.20 grams |
| Silver Oxide: | 195.00 grams |
| Monoethanolamine: | 39.08 grams |
| Distilled Water: | 107.58 grams |

To half of this solution (282.03 grams) is added 7.34 grams of cesium sulfate standard solution containing 0.035 grams cesium per gram solution. This solution with promoter is used initially to prepare a catalyst on carrier AA, and portions from the drained solution are used to prepare catalysts XV and XVII.

Catalyst XV is prepared by first impregnating 20.56 grams of carrier AF with 50 milliliters (71.94 grams) of the above drained solution followed by roasting as described in Examples 79 and 80. Then another identical impregnation is repeated with the roasted catalyst. The total silver pick up is 25.24 wt. % and the total promoter pick up is 711 ppm cesium.

Catalyst XVI is prepared similar to catalyst XV by first impregnating 20.64 grams of carrier AG with 72.3 grams of the drained solution followed by roasting. Then the roasted catalyst is impregnated for a second time with an identical procedure. The total silver pick up is 17.59 wt. % and total promoter pick up is 497 ppm cesium.

The catalysts and performances are summarized in Table 29. A microreactor using crushed catalyst pills is used.

TABLE 29

| EX-AMPLE | CATA-LYST | CARRIER | Ag WT. % | WT. PPM Cs AS Cs$_2$So$_4$ | % EO | % EFF | TEMP (°C.) | CONDI-TION |
|---|---|---|---|---|---|---|---|---|
| 100 | XV | AF | 25.24 | 711 | 1.53 | 73.5 | 235 | O$_2$ |
| 101* | XVI | AG | 17.59 | 497 | 2.00 | 69.9 | 251 | O$_2$ |

*Comparative

EXAMPLES 102 TO 107

An impregnation solution is prepared which is substantially the same as that described in Examples 92 and 93, except that it contains 24.51 wt. percent silver.

Catalysts XVII, XVIII and XIX are prepared with carrier AH. For each catalyst 125 cc of carrier are impregnated with 260 grams of above solution according to procedures described in Examples 79 and 80. Appropriate amounts of Cs$_2$SO$_4$ promoter are added to each solution to provide the desired promoter (Cs) concentration on the roasted catalyst as set forth in Table 30. The excess solution drained was used with appropriate amounts of promoter as set forth in Table 30 to reimpregnate each catalyst for second time followed by a second roasting. The total amount of promoter is deposited in two stages at about 50% each impregnation.

Catalysts XX, XXI and XXII are prepared similar to catalysts XVII, XVIII and XIX but using carrier AI.

The catalysts and their performances are summarized in Table 30. The performances are evaluated at Oxygen Conditions.

TABLE 30

| EX-AMPLE | CATA-LYST | CARRIER | NO OF IMPREG-NATIONS | Ag WT. % | WT. PPM Cs AS Cs$_2$SO$_4$[a] | % EO | % EFF | TEMP (°C.) |
|---|---|---|---|---|---|---|---|---|
| 102 | XVII | AH | 2 | 31.49 | 969 | 1.00 | 80.0 | 235 |
| 103 | XVIII | AH | 2 | 31.02 | 1202 | 1.00 | 79.7 | 234 |
| 104 | XIX | AH | 2 | 31.01 | 1401 | 1.00 | 79.6 | 240 |
| 105 | XX | AI | 2 | 31.50 | 1284 | 1.00 | 79.2 | 236 |
| 106 | XXI | AI | 2 | 31.20 | 1564 | 1.00 | 80.2 | 232 |
| 107 | XXII | AI | 2 | 30.79 | 1828 | 1.00 | 79.0 | 240 |

[a]Added about 50% in each impregnation

EXAMPLES 108 TO 110 (ALL COMPARATIVE)

A solution is prepared as follows:

| | |
|---|---|
| Ethylenediamine: | 55.60 grams |
| Oxalic Acid Dihydrate: | 55.60 grams |
| Silver Oxide: | 97.54 grams |
| Monoethanolamine: | 19.54 grams |
| Distilled water: | 54.37 grams |

To one half of the above solution is added 4.61 grams of cesium sulfate standard solution containing 0.035 gram of cesium per gram of solution and 35.00 grams of water to adjust to the volume to 125 milliliters. This solution is used to prepare catalyst XXIII.

Another solution is made for preparing catalysts XXIV and XXV. The solution is prepared with:

| | |
|---|---|
| 55.60 | grams of ethylenediamine |
| 55.60 | grams of oxalic acid dihydrate |
| 97.54 | grams silver oxide |
| 19.54 | grams monoethanolamine |
| 122.00 | grams of distilled water |

The above solution is divided into equal halves. To the first half 2.85 grams of the above cesium sulfate solution are added and used to prepare catalyst XXIV. To the other half 3.42 grams of the cesium sulfate solution are added and used to prepare catalyst XXV.

The catalyst preparations are summarized in Table 31 and performances are summarized in Table 32. The performance is evaluated using crushed catalyst in a microreactor, using the procedures set forth for example 94.

TABLE 31

| First Impregnation | Catalysts | | |
|---|---|---|---|
| | XXIII | XXIV | XXV |
| Solution Wt. used (grams) | 172.48 | 176.88 | 174.67 |
| Promoter Added (grams) (as Cs$_2$SO$_4$)* | 0.1613 | 0.0996 | 0.11967 |
| Support Wt. (grams) | 60.80 | 60.02 | 60.13 |
| Vacuum (inches of Hg) | 28 | 28 | 28 |
| Evacuation Time (min) | 15 | 15 | 15 |
| Impregnation Time (min) | 60 | 60 | 60 |
| Drain Time (min) | 15 | 20 | 20 |
| Silver Pick up (wt. %) | 20.22 | 20.21 | 20.05 |
| Promoter Pick up (ppm) | 719 (Cs) | 443 (cs) | 528 (Cs) |

*Added as aqueous solution containing 0.035 gram cesium per gram solution.

TABLE 32

| Example | Catalyst | Carrier | No. of Impregnation | Ag wt. % | % EO | % Eff | Temp (°C.) | Condition |
|---|---|---|---|---|---|---|---|---|
| 108 | XXIII | AJ | 1 | 20.22 | 1.46 | 82.5 | 232 | O$_2$[a] |
| 109 | XXIV | AJ | 1 | 20.21 | 1.42 | 76.9 | 243 | O$_2$[a] |
| 110 | XXV | AJ | 1 | 20.05 | 1.46 | 80.9 | 233 | O$_2$[a] |

[a] with 8.5 ppm ECl instead of 10 ppm as usual.

EXAMPLES 111 TO 116

Catalyst XXVI is prepared with the following solution: 55.60 grams of ethylenediamine, 55.00 grams of distilled water, 55.60 grams of oxalic acid dihydrate, 97.54 grams of silver oxide, and 19.54 grams of monoethanolamine. This solution is divided into two equal portions, and to the first half is added 2.24 grams of a cesium sulfate standard solution containing 0.035 gram of Cs/gram solution, and additional 37.00 grams of distilled water is added to adjust the volume to 125 ml. 61.54 grams of carrier AJ are impregnated with this 125 ml solution and roasted as in Examples 79 and 80. The silver pick up is 20.22 wt. % and the promoter pick up is 350 ppm cesium.

To the second half from the above solution is added 2.75 grams of the above cesium sulfate standard solution and 36.00 grams of distilled water. This solution is used to impregnate the roasted catalyst from the first step with substantially the identical procedure. The total silver pick up is 33.33 wt. % and the total cesium pick up is 628 ppm.

Catalysts XXVII and XXVIII are prepared as follows:

An impregnation solution is prepared containing 55.60 grams of ethylenediamine, 55.00 grams of distilled water, 55.60 grams of oxalic acid dihydrate, 97.54 grams of silver oxide and 19.54 grams of monoethanolamine. This solution is divided into two equal portsions.

To the first half of the above solution is added 2.56 grams of cesium sulfate standard solution used to make catalyst XXVI plus 37.00 grams of distilled water. 60.12 grams of carrier AJ are impregnated and roasted with this solution as in catalyst XXVI. The silver pick up is 20.06 wt. % and the cesium pickup is 396 ppm. A 49.00 ml portion (69.4 grams) from the drained solution is used to impregnate the catalyst for a second time with the incipient wetness (pore volume) method and the roasting step is identical to the first roast. The total silver pick up is 33.45 wt. % and the total promoter pick up is 641 ppm cesium. This catalyst is catalyst XXVII.

Catalyst XXVIII is prepared with the other half of the above solution to which is added 3.84 grams of the cesium sulfate standard solution used above, plus 37.00 grams of distilled water. 60.13 grams of carrier AJ are used for impregnation and roasting. The silver pick up is 19.70 wt. % and the promoter pick up is 584 ppm cesium. 67.14 grams of the drained solution are used to impregnate the catalyst for the second time as was done with catalyst XXVII with the pore volume (incipient wetness) method. The total silver pick up is 32.06 wt. % and the total promoter pick up is 950 ppm cesium.

The catalysts and their performances are summarized in Table 33.

TABLE 33

| Example | Catalyst | Carrier | No. of Impregnation | Ag (wt. %) 1st Impreg. | Ag (wt. %) Total | Cs (ppm) 1st Impreg. | Cs (ppm) Total | Method[b] | % EO | % Eff | Temp (°C.) | Reactor Type[c] | Condition |
|---|---|---|---|---|---|---|---|---|---|---|---|---|---|
| 111 | XXVI | AJ | 2 | 20.22 | 33.33 | 350 | 628 | 1 | 1.42 | 80.1 | 223 | MR | O$_2$[a] |
| 112 | XXVI | AJ | 2 | 20.22 | 33.33 | 350 | 628 | 1 | 1.00 | 78.9 | 241 | AC | Air |

TABLE 33-continued

| Example | Catalyst | Carrier | No. of Impregnation | Ag (wt. %) 1st Impreg. | Ag (wt. %) Total | Cs (ppm) 1st Impreg. | Cs (ppm) Total | Method[b] | % EO | % Eff | Temp (°C.) | Reactor Type[c] | Condition |
|---|---|---|---|---|---|---|---|---|---|---|---|---|---|
| 113 | XXVII | AJ | 2 | 20.06 | 33.45 | 396 | 641 | 2 | 1.40 | 75.7 | 248 | AC | Air |
| | | | | | | | | | 1.36 | 81.0 | 217 | MR | $O_2^{a)}$ |
| 114 | XXVII | AJ | 2 | 20.06 | 33.45 | 396 | 641 | 2 | 1.00 | 77.1 | 244 | AC | Air |
| | | | | | | | | | 1.40 | 72.2 | 253 | AC | Air |
| 115 | XXVIII | AJ | 2 | 19.70 | 32.06 | 584 | 950 | 2 | 1.40 | 81.9 | 218 | MR | $O_2^{a)}$ |
| 116 | XXVIII | AJ | 2 | 19.70 | 32.06 | 584 | 950 | 2 | 1.00 | 77.2 | 251 | AC | Air |
| | | | | | | | | | 1.40 | 74.0 | 257 | AC | Air |

[a] with 7 ppm ECl instead of standard value of 10 ppm.
[b] Method 2: two impregnations, 1st) standard with about 50% of promoter, 2nd) pore volume (incipient wetness) method with 50% of promoter. Method 1: two standard impregnations, with about 50% of the promoter added in each.
[c] MR is a microreactor using crushed catalyst, AC is an autoclave reactor. The microreactor conditions are as set forth for Example 94.

EXAMPLE 117

Catalyst XXIX is made with carrier AK using portions of the impregnating solution used in Examples 102 to 107.

84.84 grams (125 ml) of carrier AK is evacuated to 30 inch Hg vacuum for 15 minutes followed by impregnation with 268.15 grams of the above solution for 30 minutes. The catalyst is drained for 15 minutes and roasted at 500° C. for 2.5 minutes on a belt roaster (66.7 SCFH/in² air flow). The silver pick up is 15.18 wt. %.

This roasted catalyst is impregnated for a second time with the drained solution from the first impregnation to which 5.2232 grams of cesium sulfate standard solution containing 0.0383 gram cesium per gram solution are added. The impregnation and roasting are substantially identical to that used for the first impregnation. The total silver pick up is 25.73 wt. %, and total promoter pick up is 511 ppm cesium.

The catalyst performance data are summarized in Table 34.

TABLE 34

| Example | % EO | % Eff | Temp (°C.) | Reactor Condition |
|---|---|---|---|---|
| 117 | 1.00 | 77.9 | 242 | Air |
| | 1.40 | 75.4 | 255 | Air |

EXAMPLES 118 TO 120

Catalysts XXX, XXXI and XXXII are prepared as follows:

Catalyst XXX is prepared with 2183 grams of carrier AA which is impregnated twice. The first impregnation is with 7075 grams of a solution with the following composition: 1112.00 grams of ethylenediamine, 1112.00 grams of oxalic acid dihydrate, 1950.00 grams of silver oxide, 390.80 grams of monoethanolamine, 6.919 grams of cesium sulfate powder, and 2510.00 grams of distilled water. The impregnation and drain times are 60 and 30 min. respectively. The carrier is roasted at 500° C. for 2.5 min. on a belt roaster with 66.5 SCFH/in² air. The silver pick up is 19.48 wt. % and the promoter pick up is 546 ppm cesium.

A substantially identical solution to above except with 8.8700 grams of cesium sulfate powder is prepared and used to impregnate the carrier for a second time with a substantially identical procedure to that used for the first impregnation. The total silver pick up is 31.80 wt. % and the total promoter pick up is 917 ppm cesium.

Catalyst XXXI is prepared with the same impregnation solution used for catalysts XVII, XVIII, XIX, XX, and XXI in Examples 102 to 107. 2478 grams of carrier AA are impregnated with 6347 grams of the above solution with no added cesium sulfate using a procedure similar to the first impregnation of catalyst XXX above. The silver pick up is 18.19 wt. %. The drained solution is used for the second impregnation of the carrier. To this drained solution is added 8.0897 grams of cesium sulfate powder and more impregnation solution to obtain total weight of 6298 grams prior to impregnation. The procedure for impregnation and roasting is the same as that for the first impregnation. The total silver pick up is 30.50 wt. % and the total promoter pick up is 781 ppm cesium.

Catalyst XXXII is prepared with a solution containing: 55.60 grams of ethylenediamine, 55.00 grams of distilled water, 55.60 grams of oxalic acid dihydrate, 97.54 grams of silver oxide, and 19.54 grams of monoethanolamine. To half of this solution are added 3.21 grams of the cesium sulfate standard solution containing 0.035 gram of Cs/gram solution plus 37.00 grams of distilled water, and the solution is then used to impregnate 60.20 grams of carrier AA. The carrier is evacuated for 15 minutes and impregnated for 60 minutes followed by 20 minutes draining and is roasted at 500° C. for 2.5 minutes on a belt roaster with 66.5 SCFH/in² air. The silver pick up is 19.96 wt. % and the promoter pick up is 494 ppm cesium. The second half of the solution to which is added 3.93 grams of the above cesium sulfate standard solution plus 37.00 grams of distilled water, is used for the second impregnation with a substantially identical procedure to that for the first impregnation. The total silver pick up is 32.97 wt. % and the total promoter pick up is 796 ppm cesium.

Table 35 summarizes the preparations and performances of the catalysts.

TABLE 35

| Example | Catalyst | Carrier | No. of Impregnation | Ag (wt. %) 1st Impreg. | Ag (wt. %) Total* | Cs (ppm) 1st Impreg. | Cs (ppm) Total* | Method[a] | % EO | % Eff | Temp (°C.) | Condition |
|---|---|---|---|---|---|---|---|---|---|---|---|---|
| 118 | XXX | AA | 2 | 19.48 | 31.80 | 546 | 917 | 1 | 1.00 | 81.5 | 234 | $O_2$ |
| 119 | XXXI | AA | 2 | 18.19 | 30.50 | 0 | 814 | 3 | 1.00 | 77.4 | 245 | Air |
| | | | | | | | | | 1.40 | 75.2 | 257 | Air |
| | | | | | | | | | 1.70 | 72.2 | 266 | Air |
| 120 | XXXII | AA | 2 | 19.96 | 32.97 | 494 | 796 | 1 | 1.40 | 76.1 | 251 | Air |

TABLE 35-continued

| Example | Catalyst | Carrier | No. of Impregnation | Ag (wt. %) 1st Impreg. | Ag (wt. %) Total* | Cs (ppm) 1st Impreg. | Cs (ppm) Total* | Method[a] | % EO | % Eff | Temp (°C.) | Condition |
|---|---|---|---|---|---|---|---|---|---|---|---|---|
| | | | | | | | | | 1.70 | 72.6 | 260 | Air |

[a]Method 1: Two standard impregnations, with about 50% of the promoter added in each. Method 3: All the promoter is added during the second impregnation only.
*Analyzed values

EXAMPLES 121 TO 123

The following general procedure is used to prepare catalysts XXXIII to XXXV.

To a 100 ml Pyrex beaker with constant stirring are added:
7.5 grams ethylenediamine,
7.0 ml water,
7.51 grams oxalic acid,
13.16 grams silver oxide, and
2.63 grams monoethanolamine.

The beaker is covered with a watch glass between additions. The temperature of the solution after each addition ranges from 25° C. to 60° C. This mixture is then diluted with distilled water to 35 milliliters.

A cesium perrhenate standard solution containing 0.00531 gram of cesium per gram of solution is prepared by adding an equimolar amount of cesium hydroxide and ammonium perrhenate to distilled water. A cesium sulfate standard solution containing 0.015 gram of cesium per gram of solution is prepared by adding cesium sulfate to distilled water.

The standard solutions are added to the silver oxide-containing solution to provide the sought impregnating solution. The cesium perrhenate solution is heated to 75° C. to assure that the salt is dissolved, and the impregnating solution is warmed to about 40° C. to assure that the cesium perrhenate is dissolved.

Ten grams of support are added to a Pyrex impregnating chamber. The pressure of the chamber is reduced to about 2.0–5.0 mm Hg. The impregnating solution is slowly added to the chamber. The pressure of the chamber is allowed to rise back to atmospheric. The impregnating solution is drained after 20 minutes. The drained solution is retained in a covered beaker. The impregnated support is calcined in a roaster at 500° C. for 3 minutes. The impregnating and calcining steps are repeated using the drained solution for impregnation.

Table 36 summarizes the catalysts.

| Example No. | Silver wt % | Cs, ppm | Anion | Carrier |
|---|---|---|---|---|
| XXXIII | 30* | 395 | ReO$_4$ | AA |
| | | 592 | SO$_4$ | |
| XXXIV | 30* | 390 | ReO$_4$ | AA |
| | | 592 | SO$_4$ | |
| | | 160 | MnO$_4$ | |
| XXXV | 30* | 396 | ReO$_4$ | AA |
| | | 594 | SO$_4$ | |
| | | 330 | MnO$_4$ | |

Catalysts XXXIII, XXXIV and XXXV are used in a microreactor to evaluate performance. For the microreactor test, catalyst pills are crushed with a mortar and pestle and screened to the desired size (30–70 mesh). Two grams of crushed catalyst are loaded into a ¼ inch diameter by 5½ inch long stainless steel tube. The tube is placed inside a test oven and connected to a gas feed system. The temperature of the oven is controlled by a temperature controller and the reactor outlet pressure is controlled at 150 psig by a Groves back pressure regulator. The gas flow rate is adjusted to the desired gas hourly space velocity (12 liters per hour at standard temperature and pressure). The reaction temperature is measured with two thermocouples inside the reactor. One is immersed in the catalyst bed, about two inches down from the top of the reactor, and the other is located at the reactor outlet. The average of the two readings is recorded as the reaction temperature. The feed composition comprises 30 volume percent ethylene, 8 volume percent oxygen, 6.5 volume percent carbon dioxide, ethane and chlorides as noted in Table 37, and nitrogen as the balance of the gas.

TABLE 37

| | Catalyst XXXIII | | | Catalyst XXXIV | | | Catalyst XXXV | | | | |
|---|---|---|---|---|---|---|---|---|---|---|---|
| Day | ΔEO % | Efficiency % | Temp °C. | ΔEO % | Efficiency % | Temp °C. | ΔEO % | Efficiency % | Temp °C. | Ethane, % | Ethyl chloride, ppm |
| 1 | 1.0 | 87.9/86.0[a] | 229 | 1.1 | 87.2 | 225 | 1.2 | 85.4 | 219 | 0.72 | 3.6 |
| 2 | — | — | — | 1.2 | 85.9 | 224 | 1.2 | 83.9 | 219 | 0.53 | 5.4 |
| 3 | 1.6 | 86.1 | 226 | 1.8 | 84.4 | 234 | 1.8 | 82.9 | 228 | 0.53 | 5.4 |
| 4 | 1.9 | 85.6 | 231 | 2.0 | 83.4 | 237 | 2.0 | 82.4 | 232 | 0.50 | 7.3 |
| 5 | 2.0 | 85.2 | 235 | 2.1 | 83.0 | 238 | 2.1 | 82.2 | 233 | 0.50 | 6.2 |
| 6 | 2.0 | 85.1 | 233 | 2.1 | 83.2 | 238 | 1.6 | 83.0 | 226 | 0.50 | 5.4 |
| 7 | 2.1 | 85.3 | 237 | 2.1 | 82.5 | 241 | 2.2 | 82.0 | 239 | 0.38 | 7.6 |
| 8 | 2.2 | 84.3 | 237 | 2.2 | 81.8 | 241 | 2.3 | 81.9 | 239 | 0.38 | 7.6 |
| 9 | 2.2 | 84.0 | 237 | 2.3 | 81.6 | 241 | 2.4 | 81.8 | 239 | 0.38 | 7.6 |
| 10 | 2.3 | 83.0 | 239 | 2.4 | 81.2 | 238 | 2.4 | 81.8 | 235 | 0.52 | 7.2 |
| 11 | 2.1 | 83.7 | 235 | 2.3 | 82.3 | 234 | 2.5 | 82.7 | 233 | 0.52 | 3.9 |
| 12 | 1.8 | 84.9 | 234 | 2.1 | 84.1 | 232 | 2.4 | 83.6 | 232 | 0.52 | 3.8 |

[a]poor mass balance

What is claimed is:

1. A method for preparing a catalyst for the manufacture of alkylene oxide by the vapor phase epoxidation of alkene comprising:

a) providing a refractory solid support having a surface area of at least about 0.7 m$^2$/g, a pore volume of at least about 0.5 cc/g, and a median pore diameter between about 1 and 25 microns, and wherein between about 10 and 25 volume percent of the pores of the support have a pore diameter between about 0.5 and 1 micron, at least about 10 volume percent of the pores of the support have a pore diameter between about 1 and 10 microns, and at least about 20 volume percent of the pores of the support have a pore volume between about 10 and 100 microns;

b) impregnating the support with a first impregnating solution containing dissolved silver compound;

c) removing the impregnated support from the first impregnating solution, said support containing silver compound, and subjecting the impregnated support to conditions which form silver metal from the silver compound;

d) impregnating the support with a second impregnating solution containing additional silver compound dissolved therein;

e) removing the impregnated support from the second impregnating solution, said support containing additional silver compound, and subjecting the impregnated support to conditions which form silver metal from the additional silver compound; and f) repeating steps (d) and (e) until the amount of silver metal contained in the support is at least 30 percent by weight based on the entire weigh of the catalyst.

2. The method of claim 1, wherein the impregnating solutions contain at least one promoter which enhances the efficiency of the catalyst.

3. The method of claim 2, wherein the promoter is present only in the last silver impregnating solution.

4. The method of claim 3, wherein the promoter comprises molybdate.

5. The method of claim 1, wherein the support is contacted with a solution containing at least one promoter which enhances the efficiency of the catalyst.

6. The method of claim 1, wherein the concentration of silver compound is greater in the second impregnating solution than in the first impregnating solution.

7. The method of claim 1, wherein after impregnating the support with the first impregnating solution but before subjecting the impregnated support to conditions which form silver metal from the silver compound, the support is rinsed with a suitable solvent to remove occluded silver compound.

8. The method of claim 1, wherein the amount of impregnated silver metal is in the range of from about 30 to about 60 percent by weight based on the total weight of catalyst.

9. The method of claim 1, wherein the amount of impregnated silver metal is in the range of from about 35 to about 45 percent by weight based on the total weight of catalyst.

10. The method of claim 1, wherein the support has a lamellate morphology.

11. The method of claim 10, wherein the support is alpha-alumina.

12. The method of claim 11, wherein the support is at least 98% pure alpha-alumina.

13. The method of claim 1, wherein the support contains a fluorine-containing substance.

14. The method of claim 13, wherein the support containing a fluorine-containing substance has a lamellate morphology.

15. The method of claim 2, wherein the promoter is a compound comprising at least one element selected from groups 3b through 7b and groups 3a through 7a of the Periodic Table of the Elements.

16. The method of claim 2 wherein the promoter comprises a cation selected from the group consisting of alkali and alkaline earth metal cation.

17. The method of claim 15 in which the promoter enhances at least one of stability, efficiency and activity of the catalyst as determined under STANDARD ETHYLENE OXIDE PROCESS CONDITIONS.

18. The method of claim 15 wherein the promoter is selected from halides and oxyanions of elements other than oxygen having an atomic number of 7 to 83 and being from the groups 3b through 7b, inclusive, and 3a through 7a, inclusive, of the Periodic Table of the Elements.

19. The method of claim 18 in which the promoter is an oxyanion comprising sulfate.

20. The method of claim 18 in which the promoter is an oxyanion comprising molybdate.

21. A catalyst for the manufacture of alkylene oxide by the vapor phase epoxidation of alkene containing at least about 30 weight percent silver impregnated in at least two impregnation steps on an inert, refractory solid support having a surface area of at least about 0.7 $m^2/g$ and a pore volume of at least about 0.5 cc/g, a median pore diameter between about 1 and 25 microns, and wherein between about 10 and 25 volume percent of the pores of the support have a pore diameter between about 0.5 and 1 micron, at least about 10 volume percent of the pores of the support have a pore diameter between about 1 and 10 microns, and at least about 20 volume percent of the pores of the support have a pore volume between about 10 and 100 microns, and a promoting amount of at least one promoter to enhance the efficiency of the catalyst, wherein the amount of silver on the support is sufficient to increase the activity of the catalyst, as determined under STANDARD ETHYLENE OXIDE PROCESS CONDITIONS, by at least about 5° C., as compared to the same catalyst but containing a lesser amount of silver.

22. The catalyst of claim 21, wherein the activity is increased by at least about 10° C.

23. The catalyst of claim 21 containing from about 30 to about 60 percent by weight silver.

24. The catalyst of claim 21 containing from about 35 to about 45 percent by weight silver.

25. The catalyst of claim 21, wherein the support has a lamellate morphology.

26. The catalyst of claim 25, wherein the support comprises alpha-alumina.

27. The catalyst of claim 26, wherein the support is at least 98% pure alpha-alumina.

28. The catalyst of claim 21, wherein the support contains a fluorine-containing substance.

29. The catalyst of claim 28, wherein the support has a lamellate morphology.

30. The catalyst of claim 21, wherein the promoter is a cationic promoter.

31. The catalyst of claim 30, wherein the cationic promoter is selected from the group consisting of potassium, rubidium, cesium and mixtures thereof.

32. The catalyst of claim 21, wherein the promoter is an anionic promoter.

33. The catalyst of claim 32 in which the anionic promoter is selected from the group consisting of halides and oxyanions of elements other than oxygen having an atomic number of 7 to 83, inclusive, and being from group 3b through 7b, inclusive, and 3a through 7a, inclusive, of the Periodic Table.

34. The catalyst of claim 33, wherein the anionic promoter is selected from the group consisting of sulfate, fluorosulfate, nitrate, manganate, vanadate, chromate, molybdate, tungstate, rhenate, cerate and mixtures thereof.

35. The catalyst of claim 34 further comprising a cationic promoter comprising at least one of alkali metal and alkaline earth metal.

36. The catalyst of claim 35, wherein the cationic promoter is selected from the group consisting of cesium, rubidium, potassium, and mixtures thereof.

* * * * *